(12) United States Patent
Ding et al.

(10) Patent No.: US 7,763,704 B2
(45) Date of Patent: Jul. 27, 2010

(54) SUSHI PEPTIDE MULTIMER

(75) Inventors: Jeak Ling Ding, Singapore (SG); Bow Ho, Singapore (SG)

(73) Assignee: National University of Singapore, Crescent (SG)

( * ) Notice: Subject to any disclaimer, the term of this patent is extended or adjusted under 35 U.S.C. 154(b) by 605 days.

(21) Appl. No.: 10/563,551

(22) PCT Filed: Jul. 2, 2004

(86) PCT No.: PCT/SG2004/000194

§ 371 (c)(1),
(2), (4) Date: Aug. 17, 2006

(87) PCT Pub. No.: WO2005/003163

PCT Pub. Date: Jan. 13, 2005

(65) Prior Publication Data

US 2008/0113906 A1    May 15, 2008

(30) Foreign Application Priority Data

Jul. 4, 2003    (CA)    .................................... 2432972

(51) Int. Cl.
*A61K 38/00*    (2006.01)
*C07K 14/00*    (2006.01)

(52) U.S. Cl. ........................ 530/300; 530/810; 435/975; 436/86; 930/280

(58) Field of Classification Search .................. None
See application file for complete search history.

(56) References Cited

U.S. PATENT DOCUMENTS 6,719,973 B1 *    4/2004    Ding et al. ................ 424/185.1

FOREIGN PATENT DOCUMENTS

| WO | 01/27289 | * | 4/2001 |
| WO | WO 01/27289 A2 | | 4/2001 |
| WO | 02/088171 | * | 11/2002 |

OTHER PUBLICATIONS

Tam et al (Eur. J. Biochem. 269:923-932, 2002).*
Tan et al (The FASEB Journal, 14:1801-1813, Sep. 2000).*
Li et al (Protein Engineering, 16(8):629-635 Aug. 2003).*
Protein Engineering, vol. 16, No. 8, pp. 629-635, 2003, C. L1 et al. "Tandem repeats of Sushi3 peptide with enhanced LPS-binding and -neutralizing activities."
Journal of Chromatography B, vol. 759, pp. 237-246, 2001, J. L. Ding et al. "High-performance affinity capture-removal of bacterial pyrogen from solutions."
The Journal of Biological Chemistry, vol. 266, No. 10, pp. 6554-6561, 1991, T. Muta et al., "An endotoxin-sensitive serine protease zymogen with a mosaic structure of complement-like, epidermal growth factor-like, and lectin-like domains."
Antimicrobial Agents and Chemotherapy, vol. 45, No. 10, pp. 2820-2825, 2001, Y. H. Yau, et al. "High therapeutic index of factor C sushi peptides: potent antimicrobials against *Pseudomonas aeruginosa*."
The FASEB Journal, vol. 14, pp. 1801-1813, 2000, N.S. Tan et al. "Definition of endotixin binding sites in horseshoe crab factor C recombinant sushi proteins and neutralization of endotoxin by sushi peptides."
Letters in Applied Microbiology, vol. 30, pp. 161-166, 2000, J.M. Mauro et al. Construction and expression of functional multi-domain polypeptides in *Escherichia coli*: expression of the *Neurospora crassa* metallothionein gene.

* cited by examiner

*Primary Examiner*—Patricia A Duffy
(74) *Attorney, Agent, or Firm*—Townsend and Townsend and Crew LLP

(57) ABSTRACT

Endotoxin, also known as lipopolysaccharides (LPS), is the major mediator of septic shock due to Gram-negative bacterial infection. Chemically synthesized S3 peptide, derived from Sushi3 domain of Factor C, which is the endotoxin-sensitive serine protease of the *limulus* coagulation cascade, binds and neutralizes LPS activity. Fluorescent tagged-S3 is shown to detect LPS-containing bacteria. For large-scale production of S3 and to mimic other pathogen-recognizing molecules, tandem multimers of the S3 gene were constructed and expressed in *E. coli*. Tetramer of S3 for example is shown to display an enhanced inhibitory effect on LPS-induced activities. An affinity matrix based on tetramer of S3 is also shown to be particularly efficient at removing LPS.

17 Claims, 4 Drawing Sheets

US 7,763,704 B2

SUSHI PEPTIDE MULTIMER

REFERENCE TO RELATED APPLICATIONS

This application claims the benefit of Canadian Patent Application No. 2,432,972, filed Jul. 4, 2003, the content of which is herein incorporated by reference.

FIELD OF INVENTION

The present invention relates to Gram-negative bacterial infection and peptides which inhibit lipopolysaccharide (LPS)-induced activities.

BACKGROUND

Sepsis remains a leading cause of death in critical care unit, and is also frequently associated with serious consequence such as multiple organ failure. Gram-negative bacterial endotoxin, also known as lipopolysaccharide (LPS), has been suggested to play a pivotal role in such septic complications (Houdijk et al, 1997). The acute phase plasma protein, LPS binding protein (LBP), binds circulating LPS to extract it from micelles, and transfer it to either soluble or membrane-bound CD14 receptor in monocytes and macrophages. The interaction of this complex with Toll-like receptors (TLRs) is thought to initiate intracellular-signaling reactions, via transcription factor NF-κB. Activation of protein kinases mediates the production of inflammatory cytokines, which contribute to septic shock. It has also been shown that in the absence of plasma LBP, the LPS is able to directly interact with CD14, yielding similar effects. Thus, treatment of endotoxaemia and sepsis would be greatly aided by blocking the activity of endotoxin and/or removing them from the body fluids of patients, as cationic peptides and analogues do (de Haas et al, 1998; Scott et al, 2000).

LPS from gram-negative bacteria induces the amoebocytes of *limulus* to aggregate and degranulate. This response underlies the important defense mechanism of *limulus* against invasion of gram-negative bacteria (Ding et al, 1995). As a molecular biosensor, Factor C can be autocatalytically activated by femtograms of LPS to trigger the coagulation cascade (Ho, 1983), suggesting that it contains high affinity LPS-binding domains. Recently, two regions of Factor C that exhibit exceptionally high LPS binding affinity were defined as the Sushi1 and Sushi3 domains (Tan et al, 2000a). Two 34-mer chemically synthesized peptides, S1 and S3, spanning the 171-204 and 268-301 amino acid residues of Factor C (GenBank Accession No. S77063), are derived from Sushi1 and Sushi3 domains, respectively. (The S3 peptide consisting of residues 268-301 of Factor C is shown in SEQ ID NO:1). Both peptides inhibit LPS-induced *limulus* amoebocyte lysate (LAL) reaction and LPS-induced hTNF-α secretion (Tan et al, 2000b). See also U.S. Pat. No. 6,719,973, the entire content of which is herein incorporated by reference. The application value of these two peptides would be boosted if they could be obtained by cost effective and large-scale methods such as recombinant expression in prokaryotic systems. However, expression of smaller peptides tends to encounter technical difficulties (Le et al, 1991; Latham, 1999).

Trace levels of endotoxin or lipopolysaccharides (LPS) cause pathophysiological reactions such as fever, changes in white blood cell counts, disseminated intravascular coagulation, hypotension, shock and death. Intensive research is being carried out to develop more sensitive techniques that are able to remove minute levels of endotoxin from pharmaceutical fluids to meet higher standards of safety (Petsch 2000). Adsorption methods have proven to be the most effective (Minobe 1982) in removing endotoxins from solutions and many methods have been developed for different target solutions with varying efficiencies. However, most of these methods are not efficient over a wide range of pH and ionic strength (Petsch 2000). In addition, there is always a compromise between protein recovery and LPS removal, such that the clearance factor is often disappointing when the LPS feed concentration is low.

SUMMARY OF THE INVENTION

In one aspect, there is described a polypeptide comprising more than one S3 peptides, in particular those peptides in tandem repeat. An example of this is rS3-4-mer (SEQ ID NO:9). In specific embodiments, the polypeptide comprises 2 to 10 S3 peptides.

In another aspect, the polypeptide of the invention has at least two of the S3 peptides separated by a linking sequence which may or may not be cleavable. In specific embodiments, the linking sequence is cleavable by protease or by acid digestion. However, not all the linking sequences in the polypeptide need be cleavable. In specific embodiments, the linking sequence comprises Asp-Pro.

In another aspect, the polypeptide of the invention consists of more than one S3 peptides, in particular those peptides in tandem repeat. In specific embodiments, the polypeptide consists 2 to 10 S3 peptides.

In another aspect, there is described the polypeptide of the invention, or S3 peptide, tagged with a detectable label. In certain embodiments, the label is detectable by fluorescence.

In another aspect, there are described DNA encoding the polypeptide of the invention, expression cassettes comprising the DNA of the invention, and vectors comprising the expression cassette of the invention.

In another aspect, there is described a host cell comprising the DNA of the invention.

In another aspect, there is described a method of producing a multimer of S3 peptide, comprising the step of expressing DNA encoding the polypeptide of the invention in a host cell. The method may further comprise the step of isolating the polypeptide.

In another aspect, there is described a method of producing a polypeptide having a desired number of S3 peptides. The method comprises the step of expressing in a host cell DNA which encodes S3 peptides in a single open reading frame, wherein the S3 peptides appear in the open reading frame in greater number than the desired number, and wherein at least two of the S3 peptides are separated by a cleavable linking sequence. The expressed polypeptide is then subjected to conditions suitable for cleaving the linking sequence to produce the polypeptide having the desired number of S3 peptides, but keeping the S3 peptides intact. The method may further comprise the step of isolating the polypeptide having the desired number of S3 peptides from the remaining cleavage products. In some embodiments, the cleavage method may be acid digestion or proteolytic digestion.

In another aspect, there is described a method of producing a polypeptide having four S3 peptides. The method comprises the step of expressing in a host cell DNA which encodes eight S3 peptides in a single open reading frame. There is at least one cleavable linking sequence which occurs between the fourth and fifth S3 peptide sequence. The expressed polypeptide is then subjected to conditions suitable for cleaving the linking sequence to produce the tetramer from the octamer, but keeping the tetramer intact. If necessary, the method may further comprise the step of isolating the tetramer from the remaining cleavage products such as monomer and uncleaved octamer. In some embodiments, the cleavage method may be acid digestion or proteolytic digestion.

In another aspect, there is described a method for detecting LPS-containing bacteria comprising the steps of contacting a sample to be tested for LPS-containing bacteria, with the polypeptide of the invention or S3 peptide and detecting binding between LPS and the polypeptide. The polypeptide of the invention or S3 peptide may be tagged with a detectable label such as a fluorescent tag.

In another aspect, there is described a method for treating endotoxaemia or sepsis comprising the step of administering the polypeptide of the invention to a patient suffering from endotoxaemia or sepsis.

In another aspect, there is described a method for detecting LPS-containing bacteria comprising the step of contacting a sample containing LPS-containing bacteria with the polypeptide or S3 peptide, wherein the polypeptide or S3 peptide is fluorescently labeled, and detecting bacteria-associated fluorescence arising from the label.

In another aspect, there is described S3 peptide or a polypeptide of the invention immobilized on a solid medium such as agarose beads.

In another aspect, there is described a method for removing LPS or LPS-containing bacteria from a sample, comprising the step of contacting the sample with the immobilized polypeptide or peptide of the invention under conditions which allow binding of LPS-containing bacteria to the polypeptide or the peptide, and obtaining the unbound material which is substantially free of LPS or LPS-containing bacteria.

The invention further encompasses commercial packages comprising the polypeptide of the invention and instructions for its use in detecting LPS-containing bacteria in a sample; or instructions for its use in treating endotoxaemia or sepsis.

The invention further encompasses commercial packages comprising S3 peptide or the polypeptide of the invention immobilized on a solid medium, and instructions for its use for removing LPS or LPS-containing bacteria from a sample.

DETAILED DESCRIPTION OF EMBODIMENTS

Figure 1:
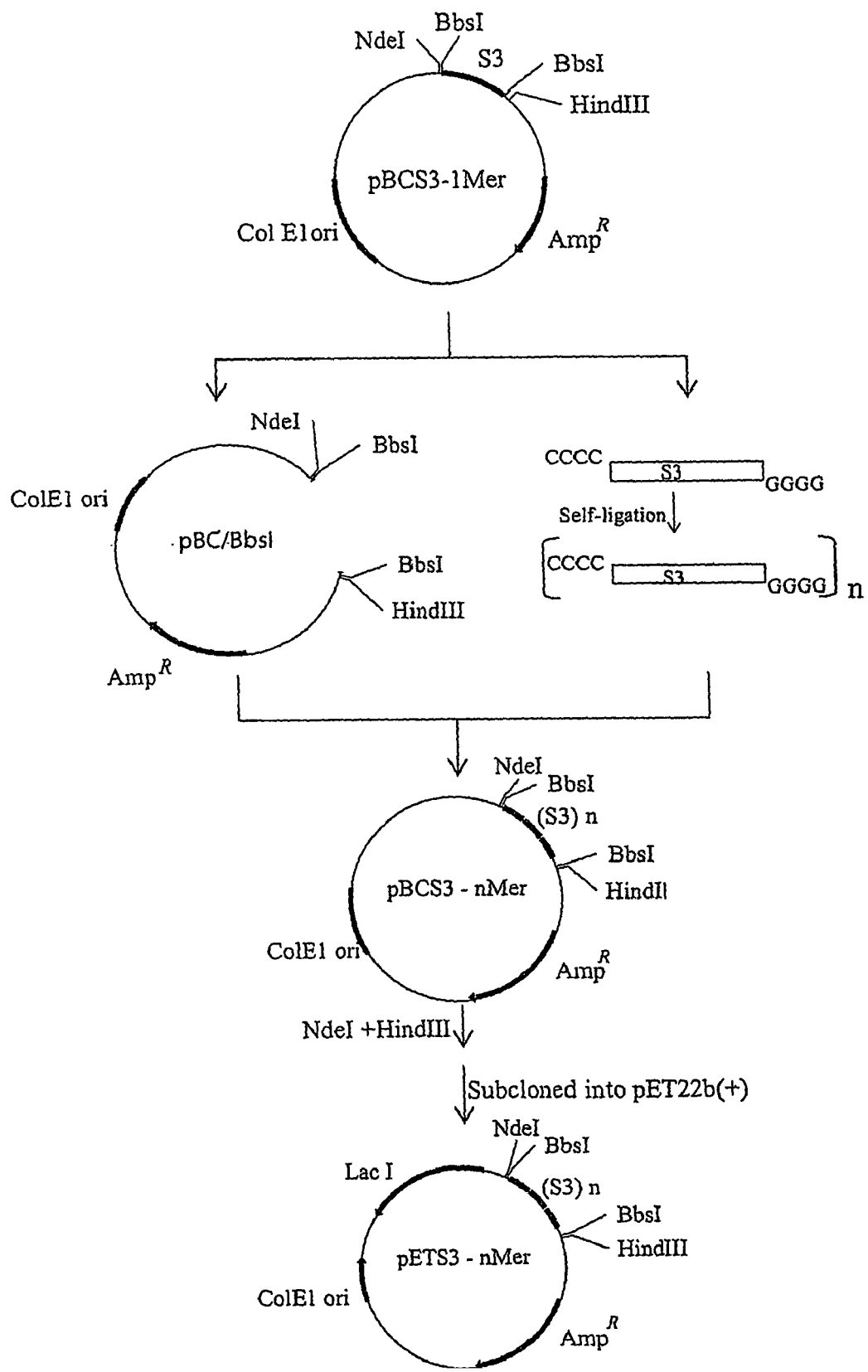
FIG. 1 shows a schematic representation of the multimerization of S3 gene using the gene amplification vector, pBC. The BbsI site was introduced into the S3 primers, and the amplified gene was cloned into pBC vector. After the BbsI digestion, the S3 gene with overhang terminals were self-ligated at 16° C. for 2 h, and inserted into pBC which was previously linearised with BbsI. The CCCC head motif on the sense strand and GGGG tail motif on anti-sense strand allowed the fragments to self-ligate directionally, giving rise to multimers of pBCS3-nMer constructs. These multimeric inserts were subsequently released and recloned into expression vector pET22b.

Before describing the present invention in further detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

S3 has been shown to be one of the LPS-binding sites of Factor C, and is able to suppress the LPS-induced cytokine production in macrophages (Tan et al, 2000b). The immobilized S3 peptide analogue can remove LPS from culture medium with high efficiency (Ding et al, 2001). Thus, this promising reagent can be applied to prevent sepsis due to circulating LPS, which is released by viable or injured Gram-negative bacteria. Chemical synthesis may be used to obtain large quantity of this peptide, but expression in *E. coli* may be more cost-effective (Latham, 1999). However, the yield from E. coli may be low and unstable (Le et al, 1991). Thus, expression of the multimers of peptides would circumvent the abovementioned problems (Kajino et al, 2000). A more important attribute for recombinant multimers of S3 is the expected enhancement in ligand-binding affinity and LPS-neutralisation activity achieved through synergistic effects of multiple LPS-binding units in one molecule (Mauro et al, 2000).

The term "isolated polynucleotide" or "isolated polypeptide" is defined as one which is removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

Many methods can be applied to construct multimers including tandem repeats of a peptide (Lee et al, 2000; Mauro, et al, 2000; Dolby, et al, 1999). Chemical synthesis, especially solid-phase synthesis may be used for short (e.g., less than 50 residues) peptides or those containing unnatural or unusual amino acids such as D-Tyr, ornithine, amino-adipic acid, and the like. Recombinant procedures are preferred for longer polypeptides.

Peptides can be synthesized chemically by such commonly used methods as t-BOC or FMOC protection of alpha-amino groups. Both methods involve stepwise syntheses whereby a single amino acid is added at each step starting from the carboxyl-terminus of the peptide (See, Coligan et al., Current Protocols in Immunology, Wiley Interscience, 1991, Unit 9). Peptides of the invention can also be synthesized by the solid phase peptide synthesis methods well known in the art. (Merrifield, J. Am. Chem. Soc., 85:2149, 1962), and Stewart and Young, Solid Phase Peptides Synthesis, Pierce, Rockford, Ill. (1984)). Peptides can be synthesized using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about 0.25 to 1 hour at 0° C. After evaporation of the reagents, the peptides are extracted from the polymer with 1% acetic acid solution which is then lyophilized to yield the crude material.

The crude material can typically be purified by such techniques as gel filtration on Sephadex G-15 using 5% acetic acid as a solvent, by high pressure liquid chromatography, and the like. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and assessed by the solid phase Edman degradation (see e.g. Protein Purification, M. P. Deutscher, ed. Methods in Enzymology, Vol 182, Academic Press, 1990). Automated synthesis using FMOC solid phase synthetic methods can be achieved using an automated peptide synthesizer (Model 432A, Applied Biosystems, Inc.). Peptides are oxidized in Trix-DMSO-isopropanol at pH 7.5 for about 15 to about 20 hours at about 23° C. to permit the formation of disulphide bonds (Tam et al. (1991) J. Am. Chem. Soc 113:6657-6662).

Following disulphide bond formation, the suspension is purified using reverse phase FPLC by which a yield of about 20% can be obtained.

The invention encompasses recombinant methods for producing a polypeptide comprising a multimer of S3. Such methods comprise the step of introducing DNA encoding the polypeptide into a host cell. If desired, the S3 multimer may be cleaved from the polypeptide.

"Amino acid cleavage site" refers to an amino acid or amino acids that serve as a recognition site for a chemical or enzymatic reaction such that the peptide chain is cleaved at that site by the chemical agent or enzyme. Amino acid cleavage sites include those at aspartic acid-proline (Asp-Pro), methionine (Met), tryptophan (Trp) or glutamic acid (Glu). "Acid-sensitive amino acid cleavage site" as used herein refers to an amino acid or amino acids that serve as a recognition site such that the peptide chain is cleaved at that site by acid. Particularly preferred is the Asp-Pro cleavage site which may be cleaved between Asp and Pro by acid hydrolysis.

Polypeptides containing the multimers of S3 may contain a linking amino acid or amino acids for cleaving the specific multimer of interest from the polypeptide. For example, a polypeptide having multiples of S3 tetramers may contain amino acid cleavage sites between the tetramers. In another embodiment, the desired S3 multimer may be produced as a fusion protein where the S3 multimer is fused to a heterologous polypeptide such as the commercially available His-tag, and where an amino acid cleavage site is placed between the S3 multimer and the heterologous polypeptide. The linking amino acid or amino acids are incorporated between the multimer of interest and the remainder of the polypeptide in such a way that one or more cleavage reactions separate each polypeptide species to the degree necessary for intended applications. In some embodiments, the linking sequence consists of one or more amino acids, up to 100 amino acids, preferably 1, 2, 3, 4, 8, 10 amino acids. It may not in every instance be necessary to cleave all, some, or any of the species within a particular polypeptide.

As used herein, a fusion polypeptide is one that contains a multimer of S3 fused at the N- or C-terminal end to a polypeptide unrelated to S3, i.e. a heterologous polypeptide. A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the S3 multimer is inserted into an expression vector in which the polynucleotide encoding the heterologous polypeptide is already present. Such vectors and instructions for their use are commercially available, e.g. the pMal-c2 or pMal-p2 system from New England Biolabs, in which the heterologous polypeptide is a maltose binding protein, the glutathione-S-transferase system of Pharmacia, or the His-Tag system available from Novagen. These and other expression systems provide convenient means for further purification of the desired S3 multimer.

Amino acids that may be used to link the S3 multimer of interest to the remainder of the polypeptide include aspartic acid-proline, asparagine-glycine, methionine, cysteine, lysine-proline, arginine-proline, isoleucine-glutamic acid-glycine-arginine (SEQ ID NO:10), and the like. Cleavage may be effected by exposure to the appropriate chemical reagent or cleaving enzyme.

It should be recognized that cleavage may not be necessary for every multimer or fusion polypeptide that is constructed. A cleavage site could be incorporated, or absent.

The invention also encompasses a method of producing a desired S3 multimer of high purity comprising the steps of transforming a compatible host with a vector suitable for expressing a fusion polypeptide containing the S3 multimer, culturing the host, isolating the fusion polypeptide by selective binding to an affinity matrix such as a carrier linked to an antibody specific for the heterologous polypeptide, and cleaving off the desired S3 multimer either directly from the carrier-bound fusion polypeptide or after desorption from the carrier.

A necessary condition to permit such cleavage of the produced polypeptide is that it contains a unique cleavage site which may be recognized and cleaved by suitable means. Such a cleavage site may be a unique amino-acid sequence recognizable by chemical or enzymatic means and located between the desired portion of the polypeptide and remainder of the fusion polypeptide to be produced. Such a specific amino acid sequence must not occur within the desired portion.

Examples of enzymatic agents include proteases, such as collagenase, which in some cases recognize the amino acid sequence $NH_2$-Pro-X-Gly-Pro-COOH, wherein X is an arbitrary amino acid residue, e.g. leucine; chymosin (rennin), which cleaves the Met-Phe bond; kallikrein B, which cleaves on the carboxyl side of Arg in X-Phe-Arg-Y; enterokinase, which recognizes the sequence X-(Asp)-Lys-Y, wherein n=2-4 (SEQ ID NO:11), and cleaves it on the carboxyl side of Lys; and thrombin which cleaves at specific arginyl bonds. Examples of chemical agents include cyanogen bromide (CNBr), which cleaves after Met; hydroxylamine, which cleaves the Asn-Z bond, wherein Z may be Gly, Leu or Ala; formic acid, which in high concentration (about 70%) specifically cleaves Asp-Pro. Thus, if the desired portion does not contain any methionine sequences, the cleavage site may be a methionine group which can be selectively cleaved by cyanogen bromide. Chemical cleaving agents may be preferred in certain cases because protease recognition sequences may be sterically hindered in the produced polypeptide.

The techniques for introducing DNA sequences coding for such amino acid cleavage sites into the DNA sequence coding for the polypeptide are well-known in the art.

As mentioned above, cleavage may be effected either with the fusion polypeptide bound to the affinity matrix or after desorption therefrom. A batch-wise procedure may be carried out as follows. The carrier having the fusion polypeptide bound thereto, e.g. IgG-Sepharose where the IgG is specific against the heterologous polypeptide, is washed with a suitable medium and then incubated with the cleaving agent, such as protease or cyanogen bromide. After removal of the carrier material having the heterologous polypeptide bound thereto, a solution containing the cleaved desired polypeptide and the cleavage agent is obtained, from which the former may be isolated and optionally further purified by techniques known in the art such as gel filtration, ion-exchange etc.

Where the fusion polypeptide comprises a protease recognition site, the cleavage procedure may be performed in the following way. The affinity matrix-bound fusion polypeptide is washed with a suitable medium, and then eluted with an appropriate agent which is as gentle as necessary to preserve the desired S3 multimer. Such an agent may, depending on the particular S3 multimer, be a pH-lowering agent such as a glycine buffer. The eluate containing the pure fusion polypeptide is then passed through a second column comprising the immobilized protease, e.g. collagenase when the cleavage site is a collagenase susceptible sequence. When passing therethrough the fusion polypeptide is cleaved into the desired S3 multimer and the heterologous polypeptide. The resulting solution is then passed through the same affinity matrix, or a different affinity matrix, to adsorb the heterologous polypeptide portion of the solution.

In one embodiment, we chose the amplification vector that readily allows us to obtain various multimers of S3 gene. Furthermore, we designed the Asp-Pro (DP) linker between the repetitive units, to afford convenient cleavage under mildly acidic buffer to release the monomers.

Studying the tandem repeats of S3 may provide explanations as to why some proteins adopt repetitive structure, and how they contribute strategically towards pathogen recognition. In one embodiment, tandem repeats of S3 gene were cloned into a modified vector, which was subsequently transferred to an expression vector, pET22b. Induced expression of the most robust tetramer clone was scaled-up. Recombinant S3 tetramer (rS3-4mer) was purified and digested into monomers (rS3-1mer) by acid treatment, and both the recombinant peptides were tested for their endotoxin binding and neutralizing activities. The rS3-1mer peptide has the additional D (asp) and P (pro) at the ends as a result of acid cleavage of the DP linker. Chemically synthesized S3 does not have these 2 extra amino acids.

The multimeric constructs exhibit different expression levels. No expression was observed with the pETS3-1mer. As the copy number increases, the expression level improved dramatically, especially with the S3 tetramer; where the expression level reached 25% of the total cell proteins. However, further doubling to 8mer reduced the expression level, suggesting that the copy number is not always proportional to the expression level for this peptide. The ELISA-based LPS binding test and SPR result show differential binding efficiencies of rS3-4mer, rS3-1mer and the chemically synthesized S3 for LPS, with highest binding achieved by rS3-4mer. Both the LAL inhibition test and suppression of TNF-α release in THP-1 cells showed that rS3-1mer works equally well as the chemically synthesized S3 peptide to neutralize LPS, while rS3-4mer displayed a 2-fold higher anti-LPS activity. However, the rS3-1mer and chemically synthesized S3 showed inconsistent results in ELISA and SPR tests.

Two major forces mediate the interaction between LPS and LPS-binding peptides. The positive charge on the peptides forms an electrostatic attraction with the negatively charged phosphate head groups of the LPS. The other is the hydrophobic interaction between them (Goh et al, 2002; Farley et al, 1988). In fact, mutation of amino acid residues of S3 aimed at introducing positive charges only achieved a slight increase in LPS-neutralizing activity (Tan et al, 2000b). Besides charge modification, little effort has been taken to enhance the LPS-binding ability of such peptides. Herein, by creating tandem repeats of the LPS-binding units instead of increasing the number of positive charges, we demonstrate a 2-fold improvement in activity of the tetramer compared to the original monomeric unit, thus providing an alternative strategy to improve the LPS-binding activity of similar peptides.

The result of secondary structure analysis by DNAMAN program (Version 4.15, Lynnon Biosoft) shows that both S1 and S3 have a distinctive structure of four regular β-sheets alternately spaced by turns and coils. We presume that this structure may be important to the interaction with LPS, and in addition, the multiple β-sheets in rS3-4mer, may form the β-barrel structure to provide better shielding of hydrophobic acyl chain of LPS (Ferguson et al, 1998).

We have developed a specific endotoxin adsorption using rS3-4mer, which is a recombinant tetramer of S3. Its high binding affinity of LPS, lower cytotoxicity and haemolytic activity showed its advantage over the synthetic amphipathic cationic peptide, S3Δ (Ding et al, 2001). rS3-4mer was covalently conjugated to DADPA immobilized agarose beads. The efficacy of this matrix to remove LPS was tested under different conditions and compared with the S3Δ matrix.

Compared to S3Δ peptide, the rS3-4mer recombinant peptide appears to be on par if not better in terms of efficiency of LPS removal. The tandem repeats of the S3 might expose strategically positioned multiple LPS-binding motifs, which produce synergistic effect for binding LPS. Both of these peptides have great potential for the pyrogen clean-up industry, as they are re-usable, non-toxic and efficient in removing trace amounts of LPS from solutions. Better systems of removing LPS from solutions will be required to meet demands of new and tighter legislations.

In one aspect, the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture. It is understood that by the term "polypeptide" includes short amino acid sequences commonly termed "peptides".

A recombinant expression system is selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli*. Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form.

One skilled in the art would readily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. The recombinant polypeptide is purified by any well-known methods that can be readily adapted by a person skilled in the art, such as fusion of the polynucleotide encoding the polypeptide or its derivative to a small affinity binding domain.

In various embodiments as described above, a polypeptide may be cleaved to obtain the desired multimer or monomer. Proteolytic cleavage can be done by methods known in the art. One method may be acid digestion. Alternatively, a proteolytic cleavage site may be introduced at the junctions so that the desired peptide can ultimately be separated from the remainder of the polypeptide. Proteolytic enzymes include, but are not limited to, factor Xa, thrombin, and enterokinase.

By "S3 multimer" is meant a polypeptide having more than one copy of S3 peptide, including multiple tandem repeats of S3 peptide. A DNA sequence encoding S3 multimer contains the S3 peptide-encoding sequence within a single open reading frame such that when expressed, S3 multimer is produced. The S3 peptide sequences may all be the same, or may correspond to different derivatives, analogs, variants such as allelic variants, and homologs of S3 peptide so long as they retain the ability to bind to LPS. Examples of S3 peptide include SEQ ID NOs: 1 and 2. An exemplary cDNA encoding Factor C of *Carcinoscorpius rotundicauda* is set forth in SEQ ID NOs: 5 and 6. SEQ ID NO:1 corresponds to amino acids 268-301 of SEQ ID NO:6.

If the S3 peptides are linked either chemically or recombinantly to a heterologous polypeptide, they may be linked to either the 5'-end, the 3'-end, or may flank the heterologous polypeptide. Further, the S3 multimer may be located at sites internal to the heterologous polypeptide.

In certain embodiments, S3 multimer may contain 2, 3, 4, 5, 6, 7, 8, 9 or 10 S3 peptide sequences. The S3 peptides may be present as direct tamdem repeats, or they may be separated by linking amino acids or cleavage sites at junctions between some of the repeats.

By "polypeptide" or "protein" is meant any chain of amino acids, regardless of length or post-translational modification (e.g., glycosylation or phosphorylation), or chemical modification, or those containing unnatural or unusual amino acids such as D-Tyr, ornithine, amino-adipic acid. Both terms are used interchangeably in the present application.

Spacer sequences may be present between the S3 moieties. The strategic placement of various spacer sequences between S3 sequences can be used to confer even greater LPS-binding. Accordingly, a selected spacer sequence may encode a wide variety of moieties such as a single amino acid linker or a sequence of two to several amino acids. Selected spacer groups may preferably provide enzyme cleavage sites so that the expressed multimer can be processed by proteolytic enzymes in vivo (by APCs, or the like).

In various embodiments, a peptide may be labeled. The peptides may be labeled at any position in the amino acid sequence, such as at the N-termini, C-termini, or at an amino acid side chain (e.g., Lys, Arg, Ser, Cys, Tyr, Glu, Asp, etc.). However, since not all side chains will be present in all of the peptides produced in the digest, labeling at the N-, or C-termini is preferred. N-terminal peptide labeling is particularly preferred.

Preferred labeling groups are fluorescent chromophores that are conventionally used as reporter groups. For example, the structurally related cyanine (Cy™) fluorescent labeling reagents, Cy3 and Cy5, may be used to produce N-terminally-tagged peptides. Incubation of the Cy3 or Cy5 monofunctional succinimide esters with the peptide will result in N-terminal labeling of the peptides. These dyes are commercially available from Amersham Pharmacia Biotech.

Alexa™ dyes marketed by Molecular Probes, Inc. may also be used. These dyes comprise a series of fluorophores with emission maxima throughout the visible spectrum. Of these, two dyes, Alexa 532 and Alexa 568 would be especially suitable. Both share a similar fluorophore and bear the same polar sulfonate and quaternary nitrogen functional groups in similar spatial orientation in the molecule. Their emission maxima are at 554 nm and 603 nm, respectively.

A variety of techniques well-known for separating peptides may be used to separate and detect the peptides and their multimers. For example, such techniques include 2D gel electrophoresis, capillary electrophoresis, isoelectric focusing and liquid chromatography, and high-performance liquid chromatography (HPLC). Reverse-phase HPLC is a routine analytical procedure in the field of protein and peptide analysis.

In reverse phase HPLC C-18 columns typically are used, although shorter-chain stationary phases provide improved resolution for larger polypeptides. Three column formats are most widely used. Analytical columns (4.6 mm I.D.) typically are eluted at flow rates of 0.5-2 mL min$^{-1}$. Narrow bore columns (1 mm I.D.) are run at approximately 0.1 mL min$^{-}$. Fused silica capillary columns (0.1-0.3 mm I.D.) are eluted a flow rates of 4 μL min$^{-1}$ and below.

In various embodiments, the polypeptides of the invention may be immobilized on solid phase media. Generally, the matrix provides a scaffold which allows the polypeptide to which it is linked to be separated from the bulk fluid. Non-limiting examples of suitable matrices include: polymers which are insoluble in water or mixtures of water and water soluble organic solvents; beaded supports such as magnetic beads, chromatographic packing supports, media and resins; porous beaded supports such as chromatographic packing supports, media and resins (e.g. anion exchange chromatography media), a cast polymer such as a membrane (e.g. polyvinylidene difluoride, Teflon, polyethylene, polypropylene or polysulfone); co-polymeric materials and gels (e.g. polyacrylamide or agarose).

In various embodiments, the polypeptides of the invention may be used therapeutically in formulations or medicaments to prevent or treat sepsis-related disease. The invention provides corresponding methods of medical treatment, in which a therapeutic dose is administered in a pharmacologically acceptable formulation, e.g. to a patient or subject in need thereof. Accordingly, the invention also provides therapeutic compositions comprising the polypeptide of the invention, and a pharmacologically acceptable excipient or carrier. In one embodiment, such compositions include the polypeptide of the invention in a therapeutically or prophylactically effective amount sufficient to treat sepsis-related conditions. The therapeutic composition may be soluble in an aqueous solution at a physiologically acceptable pH.

A "therapeutically effective amount" refers to an amount effective, at dosages and for periods of time necessary, to achieve the desired therapeutic result, such as a reduction of symptoms related to sepsis and in turn a reduction in sepsis-related disease progression. A therapeutically effective amount of the polypeptide of the invention may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the rate of sepsis onset or progression. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the polypeptide of the invention can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. the polypeptide of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, the polypeptide of the invention may be formulated with one or more additional compounds that enhance the solubility of the polypeptide.

In accordance with another aspect of the invention, therapeutic compositions of the present invention, comprising the polypeptide of the invention, may be provided in containers or commercial packages which further comprise instructions for use of the polypeptide of the invention, in the prevention and/or treatment of sepsis-related disease, or for the preparation of a medicament for prevention and/or treatment of sepsis-related disease.

The following preparative and biological examples are offered to illustrate this invention and are not to be construed in any way as limiting the scope of this invention.

EXAMPLES

LPS from *Escherichia coli* 055:B5 was purchased from Sigma (St. Louis, Mo.). LAL kinetic-QCL kit was supplied by BioWhittaker (Walkersvile, Md.). Human TNF-α kit (OptEIA ELISA) was from Pharmingen (San Diego, Calif.). CellTiter 96 Aqueous One Solution Reagent for cytotoxicity assay was purchased from Promega (Madison, Wis.). Enzymes for DNA manipulation and polymerase reactions were purchased from NEB (Beverly, Mass.). DNA purification and extraction kits were from Qiagen (Chatsworth, Calif.). Pyrogen-free water for making buffers was from Baxter (Morton Grove, Ill.). Chemically synthesized S3 peptides were made commercially according to sequence information supplied by us.

rS3-4mer is a tetramer with tandem repeat of the S3 gene. An endotoxin removing affinity matrix was developed by using 1-ethyl-3-(3-dimethylaminopropyl) carbodiimide (EDC) as a coupling agent to link rS3-4mer to DADPA-immobilized agarose gel (Pierce, USA). The rationale for choosing DADPA-immobilized agarose matrix is based on reference (Ding et al. 2001). The LAL Kinetic-QCL assay kit was from Biowhittaker, USA. LPS (*Escherichia coli* 055:B5) and sodium deoxycholate (DOC) were from Sigma. RPMI 1640 was from Gibco, BRL. Chymotrypsinogen A was purchased from Pharmacia Biotech. All other chemicals were of analytical grade from Sigma.

All materials relating to the affinity matrix studies were depyrogenated. Glassware and sodium chloride were baked at 200° C. for 4 hours. Sterile disposables were used whenever possible and were autoclaved at 121° C. for 2 hours before use. All solutions and buffers were prepared using pyrogen-free water. LPS was sonicated for 5 minutes in a 37° C. water bath prior to use, to disperse the aggregates.

(1) Construction of Multimers of S3 Gene

Using a cloned Factor C Sushi3 domain, pAC5.1Sushi3EGFP (Tan et al, 2000), the LPS-binding motif, S3, was amplified by PCR. A cloning strategy, which allows for directional multimerization and cloning is shown in FIG. 1. Briefly, the amplification vector pBBSI (Lee et al, 1997) was modified to include an NdeI site containing the start codon adjacent to BbsI site. This modified vector was named pBC. Forward primer (SEQ ID NO:3): 5'-TC GAAGACGGCCCCAG GATCCCCATGCTGAACA-CAAGG-3' was designed with BbsI restriction site (GAAGAC) followed by GGCCCC in addition to the S3 flanking sequence. On the reverse primer (SEQ ID NO:4): 5'TAGAAGACCCGGGGGTCCATCAAAGAAAGTAGT-TA-3', similar motif was also introduced. Digestion of the PCR product by BbsI would yield fragments with complementary overhang of CCCC on the sense strand and GGGG on the antisense strand, which can be used for directional multimerization and cloning. In addition, GATCCCsequence, which codes for aspartate (D) and proline (P), was introduced into the forward primer. The peptide bond between D and P can be cleaved under acidic condition (Szoka et al, 1986), thus releasing single S3 units from the recombinant multimers. In this case, the PCR products of S3 were cloned into pBC vector, and the S3 gene was released by BbsI digestion and allowed to self-ligate first, before cloning into the pBC vector, which was previously linearised with BbsI. The multimers of S3 gene were selected and identified by enzyme digestion and sequencing.

(2) Expression of the Multimers of S3 Gene in *E. coli*

To construct expression vectors bearing tandem S3 genes under the control of T7 promoter, the fragments flanked by NdeI and HindIII (containing the multimeric S3 genes) were cloned into the vector pET22b, previously linearised with NdeI and HindIII. The constructs were transformed into *E. coli* host, BL21 (DE3) for expression. The colonies were cultured overnight in LB medium with 100 µg/ml ampicillin at 37° C., then diluted 1:100 into fresh LB medium with 100 µg/ml ampicillin and grown to $OD_{600nm}$ of 0.6 before induction with 0.5 mM IPTG (Promega). The cells were harvested every h up to 12 h, and the expressed products were monitored by SDS-PAGE.

(3) Solubilization of Inclusion Bodies and Purification of rS3-4mer

One liter cultures were pelleted at 5000 g for 10 min at 4° C. and resuspended in 60 ml of lysis buffer containing 20 mM Tris-Cl, pH 8.0 and 0.5 mM DTT. The bacterial cells in the suspension were passed through French Press (Basic Z 0.75 KW Benchtop Cell Disruptor, UK) operated at 15 kpsi, for 4 rounds in order to generate >90% cell disruption. The inclusion bodies were recovered by centrifugation at 12000 g for 20 min at 4° C. and washed with 20 mM Tris-Cl buffer containing 1 M urea and 0.5%-Triton X-100. The inclusion bodies were denatured and solubilized in 20 mM Tris-Cl with 8 M urea at room temperature for 2 h. Insoluble materials were removed by centrifugation at 16000 g for 20 min, and the supernatant was filtered and purified by anion exchange using AKTA explorer (Pharmacia). Briefly, 30 ml of solubilized proteins were applied to a Q-Sepharose column (26 mm×300 mm) equilibrated with buffer A (4 M urea, 20 mM Tris-Cl, pH 6.7). After washing with 4 column volumes of buffer A, the proteins were eluted with a linear gradient of 0% to 30% buffer B (4 M urea, 20 mM Tris-Cl, pH6.7, 1 M NaCl) and the fractions were collected for SDS-PAGE analysis. The collected fractions were pooled and dialyzed in 10 kDa molecular weight cut-off (MWCO) pore size dialysis tubing (Snakeskin, Pierce), against refolding buffer A containing 50 mM glycine, pH 9.5, 10% sucrose, 1 mM EDTA, 2 M urea, at 4° C. for 16 h, followed by buffer B containing 20 mM diethanolamine, pH 9.5, 10% (w/v) sucrose, 1 mM EDTA, 4° C. for another 8 h.

(4) Monomerization of rS3-4mer (SEQ ID NO:9) into rS3-1mer (SEQ ID NO: 7) by Acid Digestion Two adjacent amino acids, aspartate and proline were added between the S3 units, so as to act as cleavable DP linkers. The renatured rS3-4mer was precipitated with 9 volumes of ethanol, frozen at −80° C. for 1 h or at −20° C. overnight. The mixture was centrifuged at 16000 g for 10 min and the pellet was washed with 90% ethanol, dried, dissolved in digestion buffer (70% formic acid, 6 M guanidine-Cl) and digested at 42° C. for 72 h. The final products were subjected to ethanol precipitation and dissolved in 20 mM Tris-Cl pH 7.3. The cleaved rS3 peptides were then dialyzed overnight against the same buffer using dialysis tubing of 1.5 kDa MWCO pore size (Sigma), thus removing the small linkers and residual salt. The endotoxin contaminant in rS3-4mer and rS3-1mer was removed by Triton X-114 phase separation (Liu et al, 1997) followed by polymyxin B affinity chromatography (Detoxi-Gel™, Pierce).

Tricine SDS-PAGE and Western blot analysis: The recombinant proteins were resolved on tricine SDS-PAGE, using 5% stacking gel and 15% separating gel, and detected by Coomassie blue staining (Schagger et al, 1987). Western analysis was performed according to the manufacturer's instruction, using ECL Western analysis system (Pierce, Ill.). The blot was probed with polyclonal rabbit anti-S3 antibody followed by goat anti-rabbit secondary antibody conjugated to horseradish peroxidase, HRP (DAKO, CA). The blots were visualised using Supersignal West Pico Chemiluminescent Substrate and exposed to X-ray film.

(5) Assays for LPS-Neutralizing Activity (a) ELISA-Based LPS Binding Assay

The polysorp 96-well plate (MaxiSorp™, Nunc) was first coated with 100 µl per well of 4 µg/ml (approximately 1 µM) of LPS diluted in pyrogen-free phosphate-buffered saline (PBS). The plate was sealed and incubated overnight at room temperature. The wells were aspirated and washed 4 times with 300 µl wash solution (PBS containing 0.05% Tween-20). The wells were blocked with wash solution containing 2% BSA for 1 h at room temperature. After washing 2 times, varying concentrations of peptides were allowed to interact with bound LPS at room temperature for 3 h. Bound peptides were detected by incubation with rabbit anti-S3 antibody and 1:2000 of goat anti-rabbit antibody conjugated with HRP. Each antibody was incubated for 2 h at 37° C. In the final step, 100 µl of substrate, ABTS (Boehringer Mannheim), was added. The absorbance was measured at 405 nm with reference wavelength at 490 nm.

(b) Endotoxin Neutralization Assay Based on Anti-LAL Test

The LAL Kinetic-QCL kit utilizes the initial part of the LPS-triggered cascade in *limulus* amoebocyte lysate to achieve an enzymatic reaction, which catalyses the release of p-nitroaniline from a synthetic substrate, producing a yellow color, which is quantifiable by absorbance at $405_{nm}$. The $ENC_{50}$ (Endotoxin Neutralization Concentration) refers to the peptide concentration required to neutralize 50% of a predetermined quantity of endotoxin. A low $ENC_{50}$ indicates high potency of the peptide for endotoxin neutralization.

In this assay, peptides of different concentrations were incubated for 1 h at 37° C. with or without an equal volume of LPS in disposable, endotoxin-free borosilicate tubes. Fifty microliters of each mixture was then dispensed into wells of a sterile microtiter plate (Nunclon™ Δsurface, Nunc). Fifty microliters of freshly reconstituted LAL reagent was dispensed into each well. The absorbance at $405_{nm}$ of each well was monitored after 45 min, and the concentration of peptides corresponding to 50% inhibition of LAL activity was designated $ENC_{50}$.

(6) Suppression of LPS-Induced hTNF-α Secretion in Human THP-1 Cells

THP-1 cells were cultured at 37° C. in a humidified environment in the presence of 5% $CO_2$. RPMI 1640 medium was supplemented with 10% fetal bovine serum (FBS), penicillin (100 U/ml), and streptomycin (100 µg/ml). The cells were maintained at a density of $2.5 \times 10^{5-6}$ cells/ml. THP-1 monocytes were transformed into macrophages by addition of phorbol myristic acid, PMA (Sigma) at a stock of 0.3 mg/ml in dimethyl sulfoxide to give a final concentration of 30 ng/ml and 0.01% dimethyl sulfoxide. PMA-treated cell suspensions were immediately plated into 96-well microtiter plate at a density of $4 \times 10^5$ cells/ml and allowed to differentiate for 48 h at 37° C. The culture medium was removed and the cells were washed twice with serum-free RPMI 1640. Thereafter, the macrophages were stimulated with 50 EU/ml LPS (a specific activity of LPS that has been standardized by LAL test against FDA-approved LPS standards), peptides alone or LPS (pre-incubated with various concentrations of peptides) and incubated at 37° C. After 6 h, the culture medium was collected and hTNF-α concentration in the supernatants was assayed using ELISA.

(7) Realtime Interaction Analysis between Peptides and LPS

Surface plasmon resonance (SPR) analysis of the real time interaction between peptides and LPS was performed with BIAcore 2000 (Pharmacia) using HPA chip (Tan et al, 2000b). The affinity constant was calculated using BIAevaluation software 3.0. The mean values were obtained from three independent experiments.

(8) Cytotoxicity of Peptides in Eukaryotic Cells.

THP-1 monocytes in 50 µl of $2 \times 10^4$ cells/ml in RPMI 1640 were mixed in a microtiter plate with 50 µl of two-fold serial dilutions of peptides ranging in concentration, and incubated for 60 min at 37° C. To determine the cytotoxicity induced by the peptides, 20 µl of CellTiter 96 Aqueous One Solution Reagent was added into each well for 90 min at 37° C. MTS [3-(4,5-dimethylthiazol-2-yl)-5-(3-carboxymethoxyphenyl)-2-(4-sulfophenyl)-2H-tetrazolium] is bioreduced by metabolically active cells into a colored formazan product that is soluble in tissue culture medium. For detection, the absorbance was measured at $490_{nm}$. To determine the ratio of cell lysis induced by the peptides, two controls were included by incubating cells in PBS containing 0.2% Tween-20 instead of medium only. This absorbance value corresponds to the background, as those cells could not metabolize MTS.

(9) Data Analysis of S3 Tandem Repeats Studies

Figure 2A:
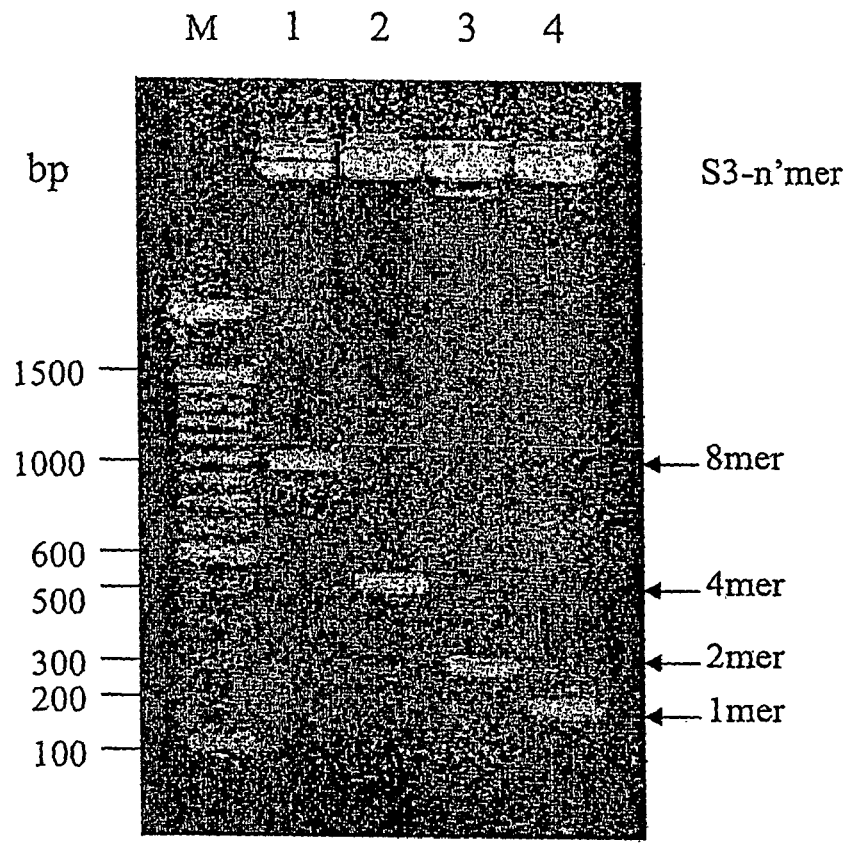
FIG. 2 shows an identification of multimers of S3 gene and expression in *E. coli*. (a) Electrophoretic analysis of the multimeric S3 genes. The number of S3 inserts cloned in the pBC was determined by digestion with NdeI and HindIII, which flank the multimers. The digests were resolved on 2% agarose gel. Lane M, 100 bp DNA ladder; lanes 1-4, NdeI and HindIII digested pBCS3-1, -2, -4, -8mer, which contain 1, 2, 4, 8 copies of S3 gene. (b) Expression of multimers of S3 gene in *E. coli* BL21. The recombinant peptides were resolved on SDS-PAGE constituting 5% stacking gel and 18% resolving gel. Lane M, peptide markers; lane 1, BL21 containing pET22b; lanes 2-5, BL21 containing S3-1, -2, -4, -8mer, respectively; lane 6, purified rS3-4mer. The arrows indicate the recombinant proteins.

Recombinant Expression of S3 Tandem Repeats, Purification and Cleavage to Monomers A 143 bp S3 gene fragment was obtained by PCR using pAC5.1Sushi3EGFP as the template. The S3 gene was cloned into pBC vector by digestion with BbsI. After multimerization, the clones containing 1, 2, 4 and 8 copies of S3 were selected (FIG. 2a) and named pBCS3-1, -2, -4, -8mer, respectively. The NdeI and HindIII-flanking fragments of these clones were inserted into pET22b for expression of the multimeric S3 gene, and the expression levels were examined by SDS-PAGE. An exemplary sequence encoding rS3-4mer is shown in SEQ ID NO:8.

Figure 2B:
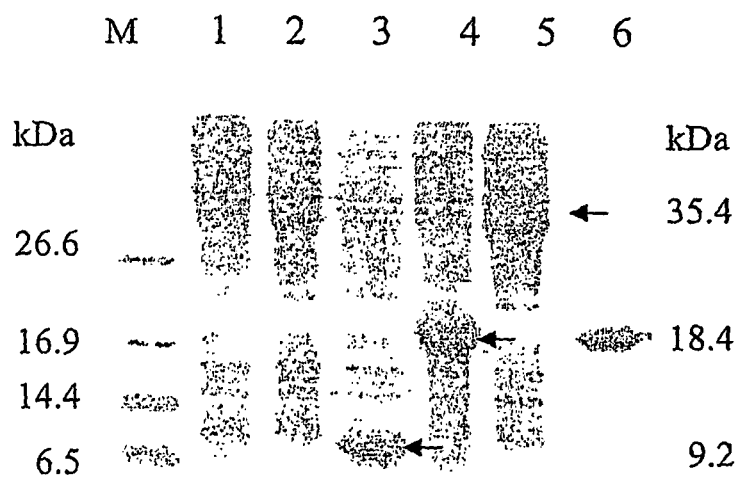

Of all the expression cassettes, the tetramer yielded the highest expression level, giving the expected recombinant S3 tetramer (rS3-4mer) of 18.4 kDa, which represented 25% of the total cell proteins (FIG. 2b). The monomer construct was not expression-competent, while the octamer construct expressed poorly.

Figure 3A:
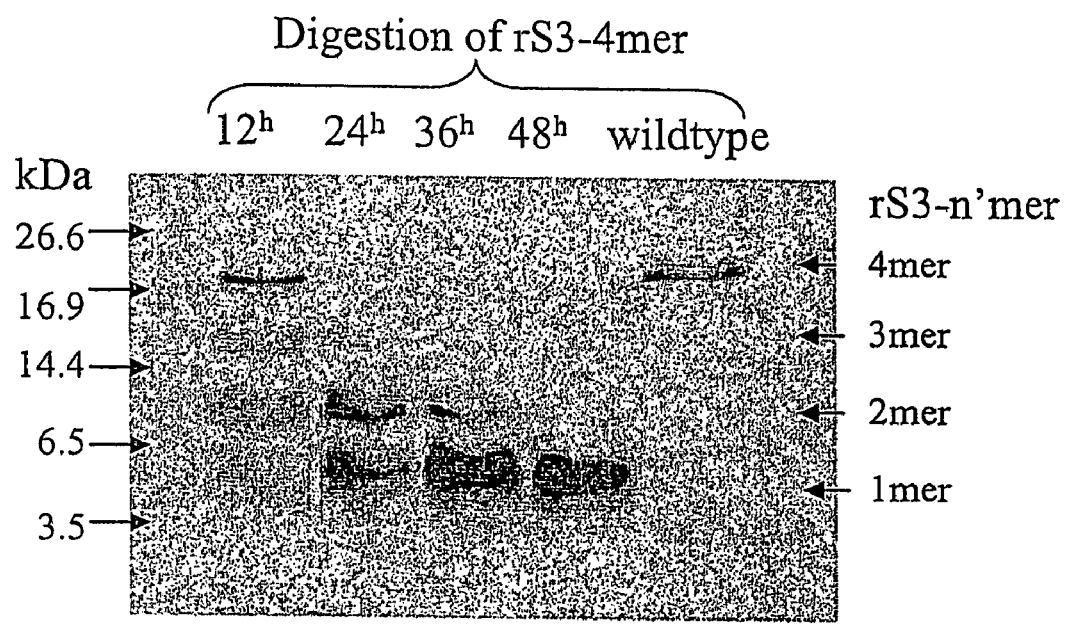
FIG. 3 shows a time course of formic acid cleavage of rS3-4mer into monomers and Western blot analysis of recombinant peptides. (a) Digestion of rS3-4mer into monomers. The rS3-4mer was dissolved in cleavage buffer and incubated at 42° C. with constant and gentle shaking. At 12, 24, 36 and 48 h, aliquots of 100 µl of samples were sampled and added to 900 µl of ethanol, chilled at −20° C. for 30 min, centrifuged at 15000 g for 10 min, and dissolved in loading buffer for electrophoretic resolution on tricine SDS-PAGE with 5% stacking gel and 15% resolving gel. Lanes 1-4 are samples digested for 12, 24, 36, 48 h, respectively; lane 5, intact rS3-4mer. (b) Western blot analysis of recombinant peptides. Lane 1, total expressed cell proteins. The expressed 18.4 kDa rS3-4mer strongly reacts with anti-S3 antibody; lane 2, partially digested peptide mixtures containing rS3-1, -2, -3, -4mer; lane 3, rS3-1mer derived from the rS3-4mer; lane 4, chemically synthesized S3 peptide. All peptides derived from rS3-4mer reacted with the antibody.

The rS3-4mer was expressed as inclusion bodies in *E. coli*. The solubilization in 8 M urea and purification through Q-Sepharose anion exchange chromatography produced more than 95% purity of rS3-4mer (FIG. 2b), yielding 42 mg rS3-4mer per liter of culture. The purified protein was dialyzed and urea was removed gradually to allow the samples to refold. Dialysis also removed unspecific small molecular weight bacteria proteins, hence further improving the purity of the rS3-4mer. SDS-PAGE under non-reducing conditions showed majority of one band with the expected size (data not shown). A minor form of a larger aggregate was removed by size exclusion using Superose® 12 column (Pharmacia). The refolded protein was precipitated with 90% ethanol and redissolved in acid digestion buffer to obtain the monomers (rS3-1mer). The process of acid digestion is time dependent. A one-day treatment yielded polymeric mixtures of four kinds of rS3 peptides: rS3-4, -3, -2, -1mer (FIG. 3a). Within 2 days, more than 90% of the multimers was cleaved to the monomers.

Recombinant Sushi3 Peptides Show Stronger Binding Potency to LPS

Figure 3B:
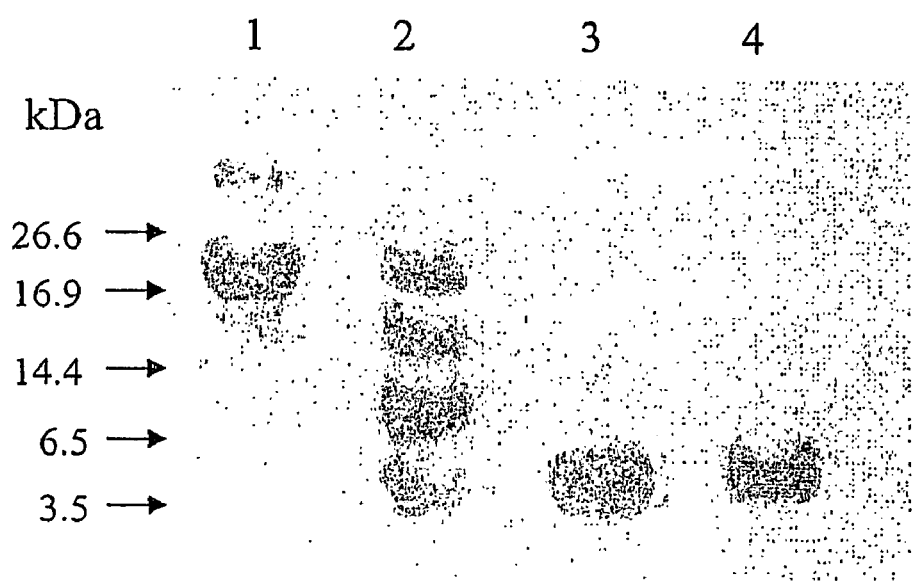

Samples from the total cell proteins, purified rS3-4mer, partially digested rS3 polymers, rS3-1mer and chemically synthesized S3 peptide were resolved on tricine SDS-PAGE and subjected to Western analysis against anti-S3 antibody. The rS3-1mer and its partially digested polymeric repeats (2, 3 and 4mers) were immunoreactive to the polyclonal rabbit anti-S3 antibody (FIG. 3b). Thus, the antibody can be employed for the ELISA-based LPS binding assay.

Figure 4:
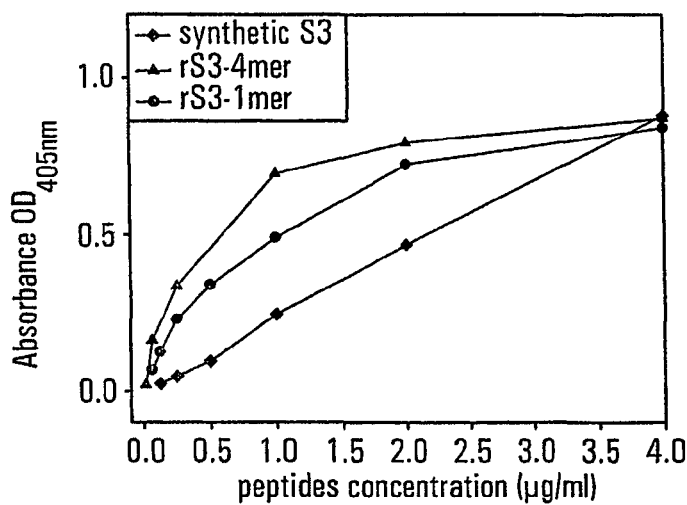
FIG. 4 shows an ELISA-based LPS binding assay. LPS was coated overnight on 96-well plates. Varying concentrations of peptides were allowed to interact with the immobilized LPS. The amount of bound peptides was determined by rabbit anti-S3 IgG and quantitated by ABTS substrate. The average $OD_{405nm}$ of the triplicate samples were calculated and plotted with the corresponding concentration.

ELISA-based LPS binding assay revealed different binding capabilities with rS3-1 mer, -4mer and chemically synthesized S3. At 4 µg/ml, both recombinant peptides reached saturation of binding to LPS (FIG. 4), while the chemically synthesized peptide continued linearly and required 20 µg/ml to reach saturation of binding with LPS (data not shown). The $EBC_{50}$ (Endotoxin Binding Concentration) of the peptide, which achieves 50% of maximum binding to LPS on the ELISA plate, reflects the binding activity of peptide to LPS, with the lower $EBC_{50}$ indicating higher potency. The rS3-4mer, rS3-1mer and chemically synthesized S3 peptides displayed $EBC_{50}$ at 0.41 µg/ml, 1.02 µg/ml and 9.74 µg/ml, respectively. The kinetics of binding of peptides to LPS in 20 mM Tris-Cl, pH7.3, was also measured by SPR analysis with BIAcore 2000 using HPA chip, which was immobilized with lipid A (bioactive moiety of LPS). The Kd values of chemically synthesized S3, rS3-1mer and rS3-4mer are $(7.80\pm2.18)\times10^{-7}$ M, $(4.74\pm2.34)\times10^{-8}$ M, $(1.71\pm1.86)\times10^{-8}$ M, respectively.

Figure 5A:
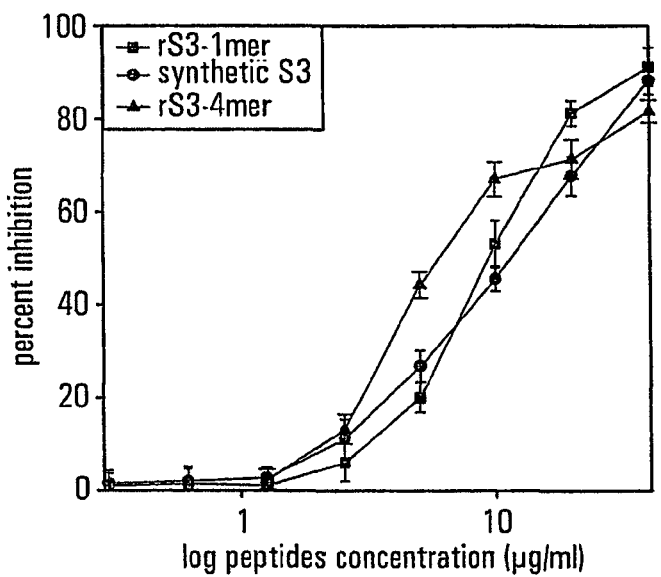
FIG. 5 shows a comparison of rS3-4mer and -1mer with chemically synthesized S3 in inhibition of LPS-induced LAL assay and hTNF-α secretion in human THP-1 cells. (a) Inhibition of LPS-induced LAL assay. Binding of the peptides to LPS would competitively inhibit the chromogenic reaction in kinetic-QCL LAL test. The $ENC_{50}$ values of rS3-4, rS3-1mer and chemically synthesized S3 peptide were determined to be 5.4 µg/ml, 9.2 µg/ml, 10.2 µg/ml, respectively. (b) Suppression of LPS-induced hTNF-α secretion in human THP-1 cells. The rS3-4mer and rS3-1mer were tested for their ability to suppress LPS-induced hTNF-α secretion from THP.1 cells. Both peptides inhibit hTNF-α production in a dose-dependent manner, albeit with different efficiency. rS3-4mer required only 40.4 µg/ml to achieve $ENC_{50}$, compared to 83.2 µg/ml needed for rS3-1mer. The decrease in TNF-α secretion was expressed as percentage of control (LPS only).

The Recombinant S3 Peptides Inhibit Endotoxin-Induced LAL Reaction and hTNF-α Release from THP-1 Cells The 50% endotoxin-neutralizing concentration ($ENC_{50}$) value of the peptides against 5 EU/ml of LPS was determined to be 5.4 µg/ml for rS3-4mer, 9.2 µg/ml for rS3-1mer, and 10.2 µg/ml for chemically synthesized S3 (FIG. 5a). A lower $ENC_{50}$ indicates higher potency of endotoxin neutralization. The binding isotherm of the two monomeric peptides, whether it is recombinant or synthetic is similar, but rS3-4mer shows a 2-fold stronger LPS neutralization efficacy.

Figure 5B:
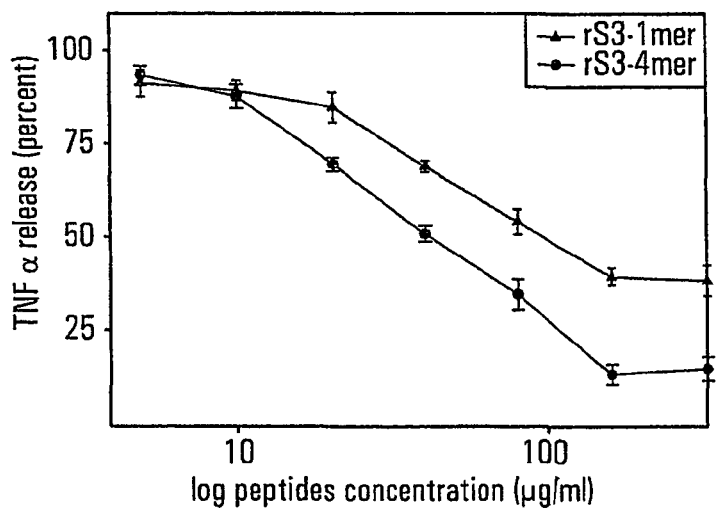

Similar results were also obtained by measuring the ability of rS3-4mer & -1mer to inhibit LPS-induced hTNF-α production by THP-1 cells, which were incubated with 50 EU/ml of LPS containing various concentrations of peptides. As shown in FIG. 5b, rS3-1mer required 83.2 µg/ml, whereas rS3-4mer required 40.4 µg/ml to achieve 50% inhibition.

The Peptides Show Minimal Cytotoxicity to Eukaryotic Cells

Both recombinant peptides had minimal effect on cell permeabilization. At the highest concentration of 50 µM, only 2-3% of cell lysis was caused by rS3-4mer, indicating that the recombinant multimers of S3 would have negligible contraindications, although the LPS binding activity is amplified significantly.

(10) Recombinant Sushi 3 Peptides (rS3) Labeled with Quantum Dot (QD) Tags Bacteria rS3 purified from recombinant bacteria, was labeled with QD (referred to as QD-rS3) was used as a novel fluorescent tag to detect the presence of bacteria. As an example to demonstrate the concept of specific tagging of certain bacteria by QD-rS3, experiments were carried out with 2 strains for gram negative bacteria (*Escherichia coli* and *Pseudomonas aeruginosa*) and a gram positive bacteria, *Staphylococcus aureus*). By addition of small quantities of QD-rS3 to overnight cultures of the bacteria, one observes, within minutes, the fluorescently labeled gram negative bacteria (which contain lipopolysaccharide, LPS to which rS3 specifically bind to) and no labeling of *S. aureus*. QD labeled rS3 is stable and emits strong fluorescence which readily biosenses the presence of gram negative bacteria.

This method can be applied to tagging bacteria in solution and in solid phase.

(11) Covalent Conjugation of rS3-4mer to DADPA-Immobilized Agarose Beads rS3-4mer affinity matrix was prepared using DADPA-immobilized agarose. The peptide was dissolved in 1 ml conjugation buffer [0.1M 2-(N-morpholino)ethanesulfonic acid (MES), pH 4.7] and used for conjugation by EDC, to DADPA-agarose packed in a column. After 3 hours of incubation, the column was drained and washed with water. These eluents were collected in 1 ml fractions. The amount of peptide immobilized to the matrix was determined by measuring the absorbance of the fractions at 280 nm.

Beads were regenerated with 10-column volumes of 1% DOC, followed by 10-column volumes of pyrogen-free water, 2 M NaCl and pyrogen-free water. When not in use, the peptide-conjugated beads were stored at 4° C. with 0.02% sodium azide to prevent the growth of bacteria.

(12) LPS Adsorption Assay

After regeneration of the column and equilibration in the appropriate buffer, the LPS-binding capacity of rS3-4mer-coupled beads was tested batchwise. An aliquot of 5 ml of standard LPS solution (under different pH and in the presence or absence of chymotrypsinogen A and EDTA) was allowed to flow through the column twice at room temperature. Solutions before and after the treatment were collected to determine the LPS removal and protein recovery. EDTA was added in order to reduce the affinity of LPS to proteins. This helps to improve the removal of low levels of LPS from protein solutions. (Petsch 2000).

(13) Quantification of LPS and Proteins

LPS was quantified by using the LAL chromogenic kinetic assay. The solutions were sonicated and diluted in borosilicate glass tubes at 37° C. Fifty μl of each mixture was carefully dispensed into appropriate wells of a sterile 96-well microtitre plate (Nunclon™ Δ surface, Nunc). The reaction mixture was then incubated for 15 minutes at 37° C. before 50 μl of LAL reagent was added. The reaction mixtures were read at 405 nm every 5 minutes with a SPECTRAmax 340 plate reader running on SOFTmax PRO version 1.2.0. The temperature was kept at 37° C. during the incubation and measuring. Five LPS standards ranging from 0.005 EU/ml to 50 EU/ml were used to calibrate the absorbance into endotoxin concentration in EU/ml. A blank using pyrogen-free water and negative controls of only the peptides in buffer solution were also set up in the assay. All samples, blank, negative control and standards were in triplicates. Pyrogen-free water was used for dilution of reagents and peptides.

The protein concentration in sample solutions of before and after treatment was determined by measuring the absorbance at 280 nm with a spectrophotometer DU 650 (Beckman).

(14) Data Analysis of LPS Affinity Studies

LPS Affinity Matrix Preparation

In preparing the rS3-4mer conjugated affinity matrix for LPS, 1.5 mg/ml of peptides was used for coupling. 1.27 mg/ml of peptides was successfully coupled onto the affinity matrix with coupling efficiency of 87% achieved, based on the following calculations:

$A_{280nm}$ before coupling (abs)=1.62

$A_{280nm}$ of fraction recovery (abs)=0.0601+0.316+ 0.0472+0.0204+0.0099+0.0033+0.0016=0.21

Total protein coupled on (abs)=1.62−0.21=1.41

Coupling efficiency=1.41/1.62=87%

LPS Binding by rS3-4mer Affinity Beads at Various Endotoxin Concentrations

It is reported that the usual LPS problematic contamination level is up to 100 EU/ml after the initial steps of purification. Thus, we tested the DADPA rS3-4mer and S3Δ column at these endotoxin concentrations. When buffer solutions containing 20 mM Tris-HCl, 100 mM NaCl and 0.5M EDTA of pH7.3 were used, both spiked levels of 5 and 500 EU/ml were reduced to below the detection limit of 0.005 EU/ml for both the columns.

However, LPS is normally found together with proteins such as in pharmaceutical fluids. Therefore, there is a need to test the protein recovery and LPS removal under such conditions. There are electrostatic and hydrophilic interactions between proteins and LPS. These interactions may reduce the efficiency of LPS removal. Very often, high protein recovery will compromise the removal of LPS from the solution and vice versa. In this work, 0.5 mg/ml of chymotrypsinogen A was spiked into the same Tris buffer and was passed through the column twice to test the ability of the conjugated agarose beads for selective removal of LPS from protein solutions.

For both the columns, the LPS-affinity beads were able to remove LPS to a concentration below the detection limit of 0.005 EU/ml. However, the rS3-4mer column appears to be able to recover more proteins compared to the S3Δ column under the current process conditions (Table 1).

TABLE 1

Removal of LPS from various solutions with problematic low levels of LPS contamination[a]

| | DADPA rS3\4mer | | | | |
|---|---|---|---|---|---|
| | Tris buffer[b] (+EDTA)[c] | | | Chym. A[b] (+EDTA)[c] | |
| Column | LPS (EU/ml) | | | | Protein recovery[e] (mg/ml) |
| Before treatment | 5 | 50 | 100 | 50 | 0.5 |

TABLE 1-continued

Removal of LPS from various solutions with problematic low levels of LPS contamination[a]

| | | | | | |
|---|---|---|---|---|---|
| After treatment | <0.005[d] | <0.005[d] | <0.005[d] | <0.005[d] | 0.4175 |
| Clearance factor (cF) | >1000 | >10000 | >20000 | >10000 | 83.5% recovered |

DADPA S3Δ

| Column | Tris buffer[b] (+EDTA)[c] LPS (EU/ml) | Chym. A[b] (+EDTA)[c] | Protein recovery[e] (mg/ml) |
|---|---|---|---|
| Before treatment | 5 | 100 | 0.5 |
| After treatment | <0.005[d] | <0.005[d] | 0.3125 |
| Clearance factor (CF) | >1000 | >20000 | 62.5% recovered |

[a]Aliquots of 5 ml of each sample solution containing LPS at indicated concentrations were passed through a column with 1 ml of affinity beads. LPS concentration of samples was measured by LAL chromogenic assay.
[b]Tris buffer: 20 mM Tris-HCl, pH 7.3 containing 100 mM NaCl; Chym. A: 0.5 mg/ml chymotrypsinogen A in same Tris buffer
[c]EDTA at stock solution of 0.5 M (pH 7.3) was added to the buffer to achieve a final concentration of 5 mM before running through column.
[d]0.005 EU/ml is the detection limit of LAL chromogenic assay.
[e]$A_{280\,nm}$ intensity of the samples before and after treatment with beads were measured to calculate the protein recovery.

Characteristics of LPS Binding by rS3-4mer Affinity Beads

To determine if the peptide is able to remove LPS under a wide range of pH, buffer solutions of different pH containing 100 mM of NaCl were tested. Increase in pH was expected to cause electrostatic interaction between the negatively charged phosphate groups of LPS and the positively charged peptides to weaken and decrease the binding capacity of the peptide (Ding et al. 2001).

We observe a significant drop in efficiency of LPS removal when the pH shifted from 5.0 to 6.0. This could be because pH of 6.0 is very near the isoelectric point of the rS3-4mer, peptide, thus causing the electrostatic interactions to weaken and hence, it loses its binding capacity for LPS. When the pH shifted from 6.0 to 7.3, the efficiency of these affinity beads was enhanced with clearance factor of more than 450. Further increase in pH causes the clearance factor to drop drastically to only 4.3, this maybe due to the increase of negative charge on peptide, so decrease the affinity of peptide to LPS, since the LPS is strongly negatively charged.

From the results, the rS3-4mer is able to remove LPS under a relatively wide range of pH, but with efficiencies highest only at around pH of 7.3 (Table 2).

TABLE 2

Removal of LPS from various solutions with problematic low levels of LPS contamination[a]

| Column | DADPA/ rS3\4mer Sodium acetate buffer[b] | | | Tris buffer[c] | | DADPA s3Δ |
|---|---|---|---|---|---|---|
| pH[d] | 5.0 | 6.0 | 7.3 | 8.5 | 7.3 | |
| Before treatment (EU/ml) | | | 500 | | | |

TABLE 2-continued

Removal of LPS from various solutions with problematic low levels of LPS contamination[a]

| Column | DADPA/ rS3\4mer Sodium acetate buffer[b] | | | Tris buffer[c] | | DADPA s3Δ |
|---|---|---|---|---|---|---|
| After treatment (EU/ml) | 4.616 | 61.38 | 1.090 | 116.84 | | 3.176 |
| Clearance factor (CF) | 108 | 8 | 459 | 4.3 | | 157 |

[a]Aliquots of 5 ml of each sample solution containing LPS at indicated concentrations were passed through a column with 1 ml of affinity beads. LPS concentration of samples was measured by LAL chromogenic assay.
[b]Sodium acetate buffer: 20 mM sodium acetate containing 100 mM NaCl;
[c]Tris buffer: 20 mM Tris-HCl containing 100 mM NaCl;
[d]pH adjusted to around 7 for LAL test by adding 5% of 1 M Tris-HCl, pH 7.3 for acidic samples and 4% 1 M NaAc, pH 5.0 for the pH 8.5 sample.
[e]Clearance Factor (CF) which reflects the efficiency of LPS removal, is obtained by dividing concentration of LPS before with after treatment.

Removal of LPS in Tissue Culture Medium

For the cell culture medium RPMI 1640, both columns were able to remove LPS from 120 EU/ml to below the detection limit of 0.005 EU/ml.

TABLE 3

Removal of LPS from culture medium with problematic low level of LPS contamination[a]

| | Medium[b] | |
|---|---|---|
| Column | DADPA rS3\4mer | DADPA S3Δ |
| Before Treatment (EU/ml) | 120 | 120 |

TABLE 3-continued

Removal of LPS from culture medium with problematic low level of LPS contamination[a]

| Column | Medium[b] | |
|---|---|---|
| | DADPA rS3\4mer | DADPA S3Δ |
| After treatment (EU/ml) | <0.005[c] | <0.005[c] |
| Clearance Factor (CF) | >24000 | >24000 |

[a]Aliquots of 5 ml of each sample solution containing LPS at indicated concentrations were passed through a column with 1 ml of affinity beads. LPS concentration of samples was measured by LAL chromogenic assay.
[b]Medium: RPMI 1640 pH 9.0
[c]0.005 EU/ml is the detection limit of LAL chromogenic assay.

REFERENCES de Haas, C. J. C., M. E. van der Tol., K. P. M. Van Kessel, J. Verhoef and J. A. G. Van Strijp. (1998) J. Immumol. 161: 3607-3615.
Ding, J. L., Navas, M. A. A. and Ho, B. (1995) Mol. Marine. Biol. Biotech., 4:90-103.
Ding, J. L., Zhu, Y., and Ho, B. (2001) J. Chromatography., 795:237-246.
Dolby, N., Dombrowski, K. E. and Wright, S. E. (1999) Protein Expres Purif. 15:146-154.
Farley, M. M., Shafer, W. M. and Spitznagel, J. K. (1988) Infect Immun. 56:1589-1592.
Ferguson, A. D., Hofmann, E., Coulton, J. W., Diederiches, K. and Welte, W. (1998) Science. 5397: 2215-2220.
Goh, Y. Y., Frecer, V., Ho, B. and Ding, J. L. (2002) Protein Eng. 15:493-502.
Ho, B. (1983) Microbios Lett. 24: 81-84.
Kajino, T., Takahashi, H., Hirai, M. and Yamada, Y. (2000) Appl Environ Microbiol. 66:304-309.
Latham, P. W. (1999) Nature Biotech. 17:755-757.
Le, H. V. and Trotta, P. P. (1991) Bioprocess Technol. 12:163-81.
Lee, J. H., Minn, I., Park, C. B. and Kim, S. C. (1998) Protein Expres Purif. 12:53-60.
Lee, S. J., Lee, J. H., Jin, H. J., Ryu, H. Y., Kim, Y., Kong, S, and Kim, K. W. (2000) Mol Cells. 10:236-240.
Liu, S. G., Tobias, R., McClure, S., Styba, G., Shi, Q. W. and Jackowski, G. (1997) Clin Biochem. 6:455-463.
Mauro, J. M. and Pazirandeh, M. (2000) Lett Appl Microbiol. 2:161-166.
S. Minobe, S., Watanabe, T., Sata, T., Tosa, T., Chibata, J. Preparation of adsorbents for pyrogen adsorption. J. Chromatography. 248 (1982) 401.
Petsch, D., Anspac, F. B. Endotoxin removal from protein solutions. J. Biotechnology. 76 (2000) 97.
Schagger, H. and von Jagow, G. (1987). Anal Biochem. 166: 368-379.
Scott, M. G., Vreugdenhil, A. C. E., Buurman, W. A., Hancock, R. E. W. and Gold, M. R. (2000) J Immunol., 164: 549-533.
Szoka, P. R., Achreiber, A. B., Chan, H. and Murthy, J. (1986) DNA. 5:11-20.
Tan, N. S., Ho, B. and Ding, J. L. (2000a) FASEB. J. 14:859-870.
Tan, N. S., Ng, M. L., Yau, Y. H., Chong, P. K., Ho, B. and Ding, J. L. (2000b). FASEB. J. 14:1801-1813.

We claim:

1. A polypeptide comprising more than one S3 peptides comprising the amino acid sequence set forth in SEQ ID No: 1, wherein at least two of the S3 peptides are separated by a linking sequence cleavable by a protease.

2. The polypeptide of claim 1 wherein the S3 peptides are in tandem repeat.

3. The polypeptide of claim 1 comprising 2 to 10 S3 peptides.

4. The polypeptide of claim 1 comprising two S3 peptides.

5. The polypeptide of claim 1 comprising three S3 peptides.

6. The polypeptide of claim 1 comprising four S3 peptides.

7. The polypeptide of claim 1 comprising eight S3 peptides.

8. A polypeptide comprising more than one S3 peptides comprising the amino acid sequence set forth in SEQ ID No: 1, wherein at least two of the S3 peptides are separated by a linking sequence cleavable by acid digestion.

9. The polypeptide of claim 8 wherein at least one of the linking sequences comprises Asp-Pro.

10. A polypeptide comprising the amino acid sequence set forth in SEQ ID NO:9, having a linking sequence cleavable by a protease.

11. The polypeptide of claim 1 wherein the more than one S3 peptide is tagged with a detectable label.

12. The polypeptide of claim 11 wherein the label is detectable by fluorescence.

13. The polypeptide of claim 1 immobilized on a solid medium.

14. The polypeptide of claim 11 immobilized on a solid medium.

15. The polypeptide of claim 14 wherein the solid medium is agarose.

16. A package comprising the polypeptide of claim 1 and instructions for its use in detecting LPS-containing bacteria in a sample.

17. A package comprising the polypeptide of claim 13 and instructions for its use for removing LPS or LPS-containing bacteria from a sample.

* * * * *

SEQUENCE LISTING

```
<160> NUMBER OF SEQ ID NOS: 11

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence:synthetic
      34-mer Sushi-3 peptide (S3 peptide), residues
      268-301 of Factor C, Sushi3 domain, LPS-binding
      motif

<400> SEQUENCE: 1

His Ala Glu His Lys Val Lys Ile Gly Val Glu Gln Lys Tyr Gly Gln
1               5                   10                  15

Phe Pro Gln Gly Thr Glu Val Thr Tyr Thr Cys Ser Gly Asn Tyr Phe
            20                  25                  30

Leu Met

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence:synthetic
      34-mer Sushi-3delta peptide (S3delta peptide)

<400> SEQUENCE: 2

His Ala Glu His Lys Val Lys Ile Lys Val Lys Gln Lys Tyr Gly Gln
```

```
                 1               5              10              15
```

Phe Pro Gln Gly Thr Glu Val Thr Tyr Thr Cys Ser Gly Asn Tyr Phe
                    20                  25                  30

Leu Met

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:LPS-binding
      motif S3 PCR amplification forward primer

<400> SEQUENCE: 3
tcgaagacgg ccccaggatc cccatgctga acacaagg                              38

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:LPS-binding
      motif S3 PCR amplification reverse primer

<400> SEQUENCE: 4
tagaagaccc gggggtccat caaagaaagt agtta                                 35

<210> SEQ ID NO 5
<211> LENGTH: 3448
<212> TYPE: DNA
<213> ORGANISM: Carcinoscorpius rotundicauda
<220> FEATURE:
<223> OTHER INFORMATION: Factor C cDNA
<220> FEATURE:
<221> NAME/KEY: CDS
<222> LOCATION: (18)..(3077)
<223> OTHER INFORMATION: Factor C

<400> SEQUENCE: 5
gtgaaggtaa cttaagt atg gtc tta gcg tcg ttt ttg gtg tct ggt tta          50
                Met Val Leu Ala Ser Phe Leu Val Ser Gly Leu
                 1               5                  10 gtt cta ggg cta cta gcc caa aaa atg cgc cca gtt cag tcc aaa gga        98
Val Leu Gly Leu Leu Ala Gln Lys Met Arg Pro Val Gln Ser Lys Gly
            15                  20                  25 gta gat cta ggc ttg tgt gat gaa acg agg ttc gag tgt aag tgt ggc        146
Val Asp Leu Gly Leu Cys Asp Glu Thr Arg Phe Glu Cys Lys Cys Gly
        30                  35                  40 gat cca ggc tat gtg ttc aac att cca gtg aaa caa tgt aca tac ttt        194
Asp Pro Gly Tyr Val Phe Asn Ile Pro Val Lys Gln Cys Thr Tyr Phe
    45                  50                  55 tat cga tgg agg ccg tat tgt aaa cca tgt gat gac ctg gag gct aag        242
Tyr Arg Trp Arg Pro Tyr Cys Lys Pro Cys Asp Asp Leu Glu Ala Lys
60                  65                  70                  75 gat att tgt cca aag tac aaa cga tgt caa gag tgt aag gct ggt ctt        290
Asp Ile Cys Pro Lys Tyr Lys Arg Cys Gln Glu Cys Lys Ala Gly Leu
                80                  85                  90 gat agt tgt gtt act tgt cca cct aac aaa tat ggt act tgg tgt agc        338
Asp Ser Cys Val Thr Cys Pro Pro Asn Lys Tyr Gly Thr Trp Cys Ser
            95                 100                 105 ggt gaa tgt cag tgt aag aat gga ggt atc tgt gac cag agg aca gga        386
Gly Glu Cys Gln Cys Lys Asn Gly Gly Ile Cys Asp Gln Arg Thr Gly
       110                 115                 120

```
gct tgt gca tgt cgt gac aga tat gaa ggg gtg cac tgt gaa att ctc        434
Ala Cys Ala Cys Arg Asp Arg Tyr Glu Gly Val His Cys Glu Ile Leu
125             130                 135 aaa ggt tgt cct ctt ctt cca tcg gat tct cag gtt cag gaa gtc aga        482
Lys Gly Cys Pro Leu Leu Pro Ser Asp Ser Gln Val Gln Glu Val Arg
140             145                 150                 155 aat cca cca gat aat ccc caa act att gac tac agc tgt tca cca ggg        530
Asn Pro Pro Asp Asn Pro Gln Thr Ile Asp Tyr Ser Cys Ser Pro Gly
                160                 165                 170 ttc aag ctt aag ggt atg gca cga att agc tgt ctc cca aat gga cag        578
Phe Lys Leu Lys Gly Met Ala Arg Ile Ser Cys Leu Pro Asn Gly Gln
            175                 180                 185 tgg agt aac ttt cca ccc aaa tgt att cga gaa tgt gcc atg gtt tca        626
Trp Ser Asn Phe Pro Pro Lys Cys Ile Arg Glu Cys Ala Met Val Ser
        190                 195                 200 tct cca gaa cat ggg aaa gtg aat gct ctt agt ggt gat atg ata gaa        674
Ser Pro Glu His Gly Lys Val Asn Ala Leu Ser Gly Asp Met Ile Glu
    205                 210                 215 ggg gct act tta cgg ttc tca tgt gat agt ccc tac tac ttg att ggt        722
Gly Ala Thr Leu Arg Phe Ser Cys Asp Ser Pro Tyr Tyr Leu Ile Gly
220             225                 230                 235 caa gaa aca tta acc tgt cag ggt aat ggt cag tgg aat gga cag ata        770
Gln Glu Thr Leu Thr Cys Gln Gly Asn Gly Gln Trp Asn Gly Gln Ile
                240                 245                 250 cca caa tgt aag aac ttg gtc ttc tgt cct gac ctg gat cct gta aac        818
Pro Gln Cys Lys Asn Leu Val Phe Cys Pro Asp Leu Asp Pro Val Asn
            255                 260                 265 cat gct gaa cac aag gtt aaa att ggt gtg gaa caa aaa tat ggt cag        866
His Ala Glu His Lys Val Lys Ile Gly Val Glu Gln Lys Tyr Gly Gln
        270                 275                 280 ttt cct caa ggc act gaa gtg acc tat acg tgt tcg ggt aac tac ttc        914
Phe Pro Gln Gly Thr Glu Val Thr Tyr Thr Cys Ser Gly Asn Tyr Phe
    285                 290                 295 ttg atg ggt ttt gac acc tta aaa tgt aac cct gat ggg tct tgg tca        962
Leu Met Gly Phe Asp Thr Leu Lys Cys Asn Pro Asp Gly Ser Trp Ser
300             305                 310                 315 gga tca cag cca tcc tgt gtt aaa gtg gca gac aga gag gtc gac tgt       1010
Gly Ser Gln Pro Ser Cys Val Lys Val Ala Asp Arg Glu Val Asp Cys
                320                 325                 330 gac agt aaa gct gta gac ttc ttg gat gat gtt ggt gaa cct gtc agg       1058
Asp Ser Lys Ala Val Asp Phe Leu Asp Asp Val Gly Glu Pro Val Arg
            335                 340                 345 atc cac tgt cct gct ggc tgt tct ttg aca gct ggt act gtg tgg ggt       1106
Ile His Cys Pro Ala Gly Cys Ser Leu Thr Ala Gly Thr Val Trp Gly
        350                 355                 360 aca gcc ata tac cat gaa ctt tcc tca gtg tgt cgt gca gcc atc cat       1154
Thr Ala Ile Tyr His Glu Leu Ser Ser Val Cys Arg Ala Ala Ile His
    365                 370                 375 gct ggc aag ctt cca aac tct gga gga gcg gtg cat gtt gtg aac aat       1202
Ala Gly Lys Leu Pro Asn Ser Gly Gly Ala Val His Val Val Asn Asn
380             385                 390                 395 ggc ccc tac tcg gac ttt ctg ggt agt gac ctg aat ggg ata aaa tcg       1250
Gly Pro Tyr Ser Asp Phe Leu Gly Ser Asp Leu Asn Gly Ile Lys Ser
                400                 405                 410 gaa gag ttg aag tct ctt gcc cgg agt ttc cga ttc gat tat gtc cgt       1298
Glu Glu Leu Lys Ser Leu Ala Arg Ser Phe Arg Phe Asp Tyr Val Arg
            415                 420                 425 tcc tcc aca gca ggt aaa tca gga tgt cct gat gga tgg ttt gag gta       1346
Ser Ser Thr Ala Gly Lys Ser Gly Cys Pro Asp Gly Trp Phe Glu Val
        430                 435                 440
```

-continued

```
gac gag aac tgt gtg tac gtt aca tca aaa cag aga gcc tgg gaa aga       1394
Asp Glu Asn Cys Val Tyr Val Thr Ser Lys Gln Arg Ala Trp Glu Arg
    445                 450                 455 gct caa ggt gtg tgt acc aat atg gct gct cgt ctt gct gtg ctg gac       1442
Ala Gln Gly Val Cys Thr Asn Met Ala Ala Arg Leu Ala Val Leu Asp
460                 465                 470                 475 aaa gat gta att cca aat tcg ttg act gag act cta cga ggg aaa ggg       1490
Lys Asp Val Ile Pro Asn Ser Leu Thr Glu Thr Leu Arg Gly Lys Gly
                480                 485                 490 tta aca acc acg tgg ata gga ttg cac aga cta gat gct gag aag ccc       1538
Leu Thr Thr Thr Trp Ile Gly Leu His Arg Leu Asp Ala Glu Lys Pro
            495                 500                 505 ttt att tgg gag tta atg gat cgt agt aat gtg gtt ctg aat gat aac       1586
Phe Ile Trp Glu Leu Met Asp Arg Ser Asn Val Val Leu Asn Asp Asn
        510                 515                 520 cta aca ttc tgg gcc tct ggc gaa cct gga aat gaa act aac tgt gta       1634
Leu Thr Phe Trp Ala Ser Gly Glu Pro Gly Asn Glu Thr Asn Cys Val
    525                 530                 535 tat atg gac atc caa gat cag ttg cag tct gtg tgg aaa acc aag tca       1682
Tyr Met Asp Ile Gln Asp Gln Leu Gln Ser Val Trp Lys Thr Lys Ser
540                 545                 550                 555 tgt ttt cag ccc tca agt ttt gct tgc atg atg gat ctg tca gac aga       1730
Cys Phe Gln Pro Ser Ser Phe Ala Cys Met Met Asp Leu Ser Asp Arg
                560                 565                 570 aat aaa gcc aaa tgc gat gat cct gga tca ctg gaa aat gga cac gcc       1778
Asn Lys Ala Lys Cys Asp Asp Pro Gly Ser Leu Glu Asn Gly His Ala
            575                 580                 585 aca ctt cat gga caa agt att gat ggg ttc tat gct ggt tct tct ata       1826
Thr Leu His Gly Gln Ser Ile Asp Gly Phe Tyr Ala Gly Ser Ser Ile
        590                 595                 600 agg tac agc tgt gag gtt ctc cac tac ctc agt gga act gaa acc gta       1874
Arg Tyr Ser Cys Glu Val Leu His Tyr Leu Ser Gly Thr Glu Thr Val
    605                 610                 615 act tgt aca aca aat ggc aca tgg agt gct cct aaa cct cga tgt atc       1922
Thr Cys Thr Thr Asn Gly Thr Trp Ser Ala Pro Lys Pro Arg Cys Ile
620                 625                 630                 635 aaa gtc atc acc tgc caa aac ccc cct gta cca tca tat ggt tct gtg       1970
Lys Val Ile Thr Cys Gln Asn Pro Pro Val Pro Ser Tyr Gly Ser Val
                640                 645                 650 gaa atc aaa ccc cca agt cgg aca aac tcg ata agt cgt gtt ggg tca       2018
Glu Ile Lys Pro Pro Ser Arg Thr Asn Ser Ile Ser Arg Val Gly Ser
            655                 660                 665 cct ttc ttg agg ttg cca cgg tta ccc ctc cca tta gct aga gca gcc       2066
Pro Phe Leu Arg Leu Pro Arg Leu Pro Leu Pro Leu Ala Arg Ala Ala
        670                 675                 680 aaa cct cct cca aaa cct aga tcc tca caa ccc tct act gtg gac ttg       2114
Lys Pro Pro Pro Lys Pro Arg Ser Ser Gln Pro Ser Thr Val Asp Leu
    685                 690                 695 gct tct aaa gtt aaa cta cct gaa ggt cat tac cgg gta ggg tct cga       2162
Ala Ser Lys Val Lys Leu Pro Glu Gly His Tyr Arg Val Gly Ser Arg
700                 705                 710                 715 gcc atc tac acg tgc gag tcg aga tac tac gaa cta ctt gga tct caa       2210
Ala Ile Tyr Thr Cys Glu Ser Arg Tyr Tyr Glu Leu Leu Gly Ser Gln
                720                 725                 730 ggc aga aga tgt gac tct aat gga aac tgg agt ggt cgg cca gcg agc       2258
Gly Arg Arg Cys Asp Ser Asn Gly Asn Trp Ser Gly Arg Pro Ala Ser
            735                 740                 745 tgt att cca gtt tgt gga cgg tca gac tct cct cgt tct cct ttt atc       2306
Cys Ile Pro Val Cys Gly Arg Ser Asp Ser Pro Arg Ser Pro Phe Ile
```

-continued

```
                   750                 755                  760
tgg aat ggg aat tct aca gaa ata ggt cag tgg ccg tgg cag gca gga    2354
Trp Asn Gly Asn Ser Thr Glu Ile Gly Gln Trp Pro Trp Gln Ala Gly
765                 770                 775 atc tct aga tgg ctt gca gac cac aat atg tgg ttt ctc cag tgt gga    2402
Ile Ser Arg Trp Leu Ala Asp His Asn Met Trp Phe Leu Gln Cys Gly
780                 785                 790                 795 gga tct cta ttg aat gag aaa tgg atc gtc act gct gcc cac tgt gtc    2450
Gly Ser Leu Leu Asn Glu Lys Trp Ile Val Thr Ala Ala His Cys Val
                    800                 805                 810 acc tac tct gct act gct gag att att gac ccc aat cag ttt aaa atg    2498
Thr Tyr Ser Ala Thr Ala Glu Ile Ile Asp Pro Asn Gln Phe Lys Met
815                 820                 825 tat ctg ggc aag tac tac cgt gat gac agt aga gac gat gac tat gta    2546
Tyr Leu Gly Lys Tyr Tyr Arg Asp Asp Ser Arg Asp Asp Asp Tyr Val
            830                 835                 840 caa gta aga gag gct ctt gag atc cac gtg aat cct aac tac gac ccc    2594
Gln Val Arg Glu Ala Leu Glu Ile His Val Asn Pro Asn Tyr Asp Pro
845                 850                 855 ggc aat ctc aac ttt gac ata gcc cta att caa ctg aaa act cct gtt    2642
Gly Asn Leu Asn Phe Asp Ile Ala Leu Ile Gln Leu Lys Thr Pro Val
860                 865                 870                 875 act ttg aca aca cga gtc caa cca atc tgt ctg cct act gac atc aca    2690
Thr Leu Thr Thr Arg Val Gln Pro Ile Cys Leu Pro Thr Asp Ile Thr
            880                 885                 890 aca aga gaa cac ttg aag gag gga aca tta gca gtg gtg aca ggt tgg    2738
Thr Arg Glu His Leu Lys Glu Gly Thr Leu Ala Val Val Thr Gly Trp
895                 900                 905 ggt ttg aat gaa aac aac acc tat tca gag acg att caa caa gct gtg    2786
Gly Leu Asn Glu Asn Asn Thr Tyr Ser Glu Thr Ile Gln Gln Ala Val
            910                 915                 920 cta cct gtt gtt gca gcc agc acc tgt gaa gag ggg tac aag gaa gca    2834
Leu Pro Val Val Ala Ala Ser Thr Cys Glu Glu Gly Tyr Lys Glu Ala
925                 930                 935 gac tta cca ctg aca gta aca gag aac atg ttc tgt gca ggt tac aag    2882
Asp Leu Pro Leu Thr Val Thr Glu Asn Met Phe Cys Ala Gly Tyr Lys
940                 945                 950                 955 aag gga cgt tat gat gcc tgc agt ggg gac agt gga gga cct tta gtg    2930
Lys Gly Arg Tyr Asp Ala Cys Ser Gly Asp Ser Gly Gly Pro Leu Val
            960                 965                 970 ttt gct gat gat tcc cgt acc gaa agg cgg tgg gtc ttg gaa ggg att    2978
Phe Ala Asp Asp Ser Arg Thr Glu Arg Arg Trp Val Leu Glu Gly Ile
            975                 980                 985 gtc agc tgg ggc agt ccc agt gga tgt ggc aag gcg aac cag tac ggg    3026
Val Ser Trp Gly Ser Pro Ser Gly Cys Gly Lys Ala Asn Gln Tyr Gly
            990                 995                 1000 ggc ttc act aaa gtt aac gtt ttc ctg tca tgg att agg cag ttc att    3074
Gly Phe Thr Lys Val Asn Val Phe Leu Ser Trp Ile Arg Gln Phe Ile
    1005                1010                1015 tga aactgatcta aatattttaa gcatggttat aaacgtcttg tttcctatta         3127
1020 ttgctttact agtttaaccc ataagaaggt taactgggta aggcacaagg atcattgttt  3187 ctgtttgttt ttacaaatgg ttattttagt cagtgaatga aatagtatc cattgaagac   3247 tgttaccttt tattctacct ttttatatta ctatgtaagt atttgggata tcttctacac  3307 atgaaaattc tgtcattttta ccataaattt ggtttctggt gtgtgctaag tccaccagta 3367 gagaacgatg taatttttcac tagcacatga aataaatata gaacaaatct attataaact 3427
```

-continued

```
accttaaaaa aaaaaaaaaa a                                         3448
```

<210> SEQ ID NO 6
<211> LENGTH: 1019
<212> TYPE: PRT
<213> ORGANISM: Carcinoscorpius rotundicauda
<220> FEATURE:
<223> OTHER INFORMATION: Factor C

<400> SEQUENCE: 6

```
Met Val Leu Ala Ser Phe Leu Val Ser Gly Leu Val Leu Gly Leu Leu
  1               5                  10                  15

Ala Gln Lys Met Arg Pro Val Gln Ser Lys Gly Val Asp Leu Gly Leu
             20                  25                  30

Cys Asp Glu Thr Arg Phe Glu Cys Lys Cys Gly Asp Pro Gly Tyr Val
         35                  40                  45

Phe Asn Ile Pro Val Lys Gln Cys Thr Tyr Phe Tyr Arg Trp Arg Pro
     50                  55                  60

Tyr Cys Lys Pro Cys Asp Asp Leu Glu Ala Lys Asp Ile Cys Pro Lys
 65                  70                  75                  80

Tyr Lys Arg Cys Gln Glu Cys Lys Ala Gly Leu Asp Ser Cys Val Thr
                 85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Ala Cys Arg
        115                 120                 125

Asp Arg Tyr Glu Gly Val His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Met Ala Arg Ile Ser Cys Leu Pro Asn Gly Gln Trp Ser Asn Phe Pro
            180                 185                 190

Pro Lys Cys Ile Arg Glu Cys Ala Met Val Ser Ser Pro Glu His Gly
        195                 200                 205

Lys Val Asn Ala Leu Ser Gly Asp Met Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Asn Gly Gln Ile Pro Gln Cys Lys Asn
                245                 250                 255

Leu Val Phe Cys Pro Asp Leu Asp Pro Val Asn His Ala Glu His Lys
            260                 265                 270

Val Lys Ile Gly Val Glu Gln Lys Tyr Gly Gln Phe Pro Gln Gly Thr
        275                 280                 285

Glu Val Thr Tyr Thr Cys Ser Gly Asn Tyr Phe Leu Met Gly Phe Asp
    290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                325                 330                 335

Asp Phe Leu Asp Asp Val Gly Glu Pro Val Arg Ile His Cys Pro Ala
            340                 345                 350

Gly Cys Ser Leu Thr Ala Gly Thr Val Trp Gly Thr Ala Ile Tyr His
```

-continued

```
              355                 360                 365
Glu Leu Ser Ser Val Cys Arg Ala Ala Ile His Ala Gly Lys Leu Pro
370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Leu Lys Ser
                405                 410                 415

Leu Ala Arg Ser Phe Arg Phe Asp Tyr Val Arg Ser Ser Thr Ala Gly
                420                 425                 430

Lys Ser Gly Cys Pro Asp Gly Trp Phe Glu Val Asp Glu Asn Cys Val
                435                 440                 445

Tyr Val Thr Ser Lys Gln Arg Ala Trp Glu Arg Ala Gln Gly Val Cys
            450                 455                 460

Thr Asn Met Ala Ala Arg Leu Ala Val Leu Asp Lys Asp Val Ile Pro
465                 470                 475                 480

Asn Ser Leu Thr Glu Thr Leu Arg Gly Lys Gly Leu Thr Thr Thr Trp
                485                 490                 495

Ile Gly Leu His Arg Leu Asp Ala Glu Lys Pro Phe Ile Trp Glu Leu
                500                 505                 510

Met Asp Arg Ser Asn Val Val Leu Asn Asp Asn Leu Thr Phe Trp Ala
                515                 520                 525

Ser Gly Glu Pro Gly Asn Glu Thr Asn Cys Val Tyr Met Asp Ile Gln
                530                 535                 540

Asp Gln Leu Gln Ser Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Ser Leu Glu Asn Gly His Ala Thr Leu His Gly Gln
                580                 585                 590

Ser Ile Asp Gly Phe Tyr Ala Gly Ser Ser Ile Arg Tyr Ser Cys Glu
                595                 600                 605

Val Leu His Tyr Leu Ser Gly Thr Glu Thr Val Thr Cys Thr Thr Asn
610                 615                 620

Gly Thr Trp Ser Ala Pro Lys Pro Arg Cys Ile Lys Val Ile Thr Cys
625                 630                 635                 640

Gln Asn Pro Pro Val Pro Ser Tyr Gly Ser Val Glu Ile Lys Pro Pro
                645                 650                 655

Ser Arg Thr Asn Ser Ile Ser Arg Val Gly Ser Pro Phe Leu Arg Leu
                660                 665                 670

Pro Arg Leu Pro Leu Pro Leu Ala Arg Ala Lys Pro Pro Pro Lys
                675                 680                 685

Pro Arg Ser Ser Gln Pro Ser Thr Val Asp Leu Ala Ser Lys Val Lys
                690                 695                 700

Leu Pro Glu Gly His Tyr Arg Val Gly Ser Arg Ala Ile Tyr Thr Cys
705                 710                 715                 720

Glu Ser Arg Tyr Tyr Glu Leu Leu Gly Ser Gln Gly Arg Arg Cys Asp
                725                 730                 735

Ser Asn Gly Asn Trp Ser Gly Arg Pro Ala Ser Cys Ile Pro Val Cys
                740                 745                 750

Gly Arg Ser Asp Ser Pro Arg Ser Pro Phe Ile Trp Asn Gly Asn Ser
                755                 760                 765

Thr Glu Ile Gly Gln Trp Pro Trp Gln Ala Gly Ile Ser Arg Trp Leu
770                 775                 780
```

```
Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
                805                 810                 815

Ala Glu Ile Ile Asp Pro Asn Gln Phe Lys Met Tyr Leu Gly Lys Tyr
            820                 825                 830

Tyr Arg Asp Asp Ser Arg Asp Asp Tyr Val Gln Val Arg Glu Ala
        835                 840                 845

Leu Glu Ile His Val Asn Pro Asn Tyr Asp Pro Gly Asn Leu Asn Phe
    850                 855                 860

Asp Ile Ala Leu Ile Gln Leu Lys Thr Pro Val Thr Leu Thr Thr Arg
865                 870                 875                 880

Val Gln Pro Ile Cys Leu Pro Thr Asp Ile Thr Arg Glu His Leu
                885                 890                 895

Lys Glu Gly Thr Leu Ala Val Val Thr Gly Trp Gly Leu Asn Glu Asn
            900                 905                 910

Asn Thr Tyr Ser Glu Thr Ile Gln Gln Ala Val Leu Pro Val Val Ala
        915                 920                 925

Ala Ser Thr Cys Glu Glu Gly Tyr Lys Glu Ala Asp Leu Pro Leu Thr
    930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Ser
                965                 970                 975

Arg Thr Glu Arg Arg Trp Val Leu Glu Gly Ile Val Ser Trp Gly Ser
            980                 985                 990

Pro Ser Gly Cys Gly Lys Ala Asn Gln Tyr Gly Phe Thr Lys Val
        995                 1000                1005

Asn Val Phe Leu Ser Trp Ile Arg Gln Phe Ile
    1010                1015

<210> SEQ ID NO 7
<211> LENGTH: 36
<212> TYPE: PRT
<213> ORGANISM: Artificial Sequence
<220> FEATURE:
<223> OTHER INFORMATION: Description of Artificial Sequence:recombinant
      S3 monomer (rS3-1mer) peptide, with additional Pro
      and Asp at ends from acid cleavage of rS3-4mer DP
      linker

<400> SEQUENCE: 7

Pro His Ala Glu His Lys Val Lys Ile Gly Val Glu Gln Lys Tyr Gly
1               5                   10                  15

Gln Phe Pro Gln Gly Thr Glu Val Thr Tyr Thr Cys Ser Gly Asn Tyr
            20                  25                  30

Phe Leu Met Asp
        35

<210> SEQ ID NO 8
<211> LENGTH: 468
<212> TYPE: DNA
<213> ORGANISM: Artificial Sequence
<220> FEATURE:
<223> OTHER INFORMATION: Description of Artificial Sequence:recombinant
      S3 tetramer (rS3-4mer) tandem repeat peptide with
      acid cleavable DP linker between S3 units
<220> FEATURE:
<221> NAME/KEY: CDS
```

<222> LOCATION: (1)..(468)
<223> OTHER INFORMATION: rS3-4mer

<400> SEQUENCE: 8

```
ccc cag gat ccc cat gct gaa cac aag gtt aaa att ggt gtg gaa caa      48
Pro Gln Asp Pro His Ala Glu His Lys Val Lys Ile Gly Val Glu Gln
 1               5                  10                  15 aaa tat ggt cag ttt cct caa ggc act gaa gtg acc tat acg tgt tcg      96
Lys Tyr Gly Gln Phe Pro Gln Gly Thr Glu Val Thr Tyr Thr Cys Ser
             20                  25                  30 ggt aac tac ttc ttg atg gac ccc cag gat ccc cat gct gaa cac aag     144
Gly Asn Tyr Phe Leu Met Asp Pro Gln Asp Pro His Ala Glu His Lys
         35                  40                  45 gtt aaa att ggt gtg gaa caa aaa tat ggt cag ttt cct caa ggc act     192
Val Lys Ile Gly Val Glu Gln Lys Tyr Gly Gln Phe Pro Gln Gly Thr
     50                  55                  60 gaa gtg acc tat acg tgt tcg ggt aac tac ttc ttg atg gac ccc cag     240
Glu Val Thr Tyr Thr Cys Ser Gly Asn Tyr Phe Leu Met Asp Pro Gln
 65                  70                  75                  80 gat ccc cat gct gaa cac aag gtt aaa att ggt gtg gaa caa aaa tat     288
Asp Pro His Ala Glu His Lys Val Lys Ile Gly Val Glu Gln Lys Tyr
                 85                  90                  95 ggt cag ttt cct caa ggc act gaa gtg acc tat acg tgt tcg ggt aac     336
Gly Gln Phe Pro Gln Gly Thr Glu Val Thr Tyr Thr Cys Ser Gly Asn
             100                 105                 110 tac ttc ttg atg gac ccc cag gat ccc cat gct gaa cac aag gtt aaa     384
Tyr Phe Leu Met Asp Pro Gln Asp Pro His Ala Glu His Lys Val Lys
         115                 120                 125 att ggt gtg gaa caa aaa tat ggt cag ttt cct caa ggc act gaa gtg     432
Ile Gly Val Glu Gln Lys Tyr Gly Gln Phe Pro Gln Gly Thr Glu Val
     130                 135                 140 acc tat acg tgt tcg ggt aac tac ttc ttg atg gac                     468
Thr Tyr Thr Cys Ser Gly Asn Tyr Phe Leu Met Asp
145                 150                 155
```

<210> SEQ ID NO 9
<211> LENGTH: 156
<212> TYPE: PRT
<213> ORGANISM: Artificial Sequence
<220> FEATURE:
<223> OTHER INFORMATION: Description of Artificial Sequence:recombinant
    S3 tetramer (rS3-4mer) tandem repeat peptide with
    acid cleavable DP linkerbetween S3 units

<400> SEQUENCE: 9

```
Pro Gln Asp Pro His Ala Glu His Lys Val Lys Ile Gly Val Glu Gln
 1               5                  10                  15

Lys Tyr Gly Gln Phe Pro Gln Gly Thr Glu Val Thr Tyr Thr Cys Ser
             20                  25                  30

Gly Asn Tyr Phe Leu Met Asp Pro Gln Asp Pro His Ala Glu His Lys
         35                  40                  45

Val Lys Ile Gly Val Glu Gln Lys Tyr Gly Gln Phe Pro Gln Gly Thr
     50                  55                  60

Glu Val Thr Tyr Thr Cys Ser Gly Asn Tyr Phe Leu Met Asp Pro Gln
 65                  70                  75                  80

Asp Pro His Ala Glu His Lys Val Lys Ile Gly Val Glu Gln Lys Tyr
                 85                  90                  95

Gly Gln Phe Pro Gln Gly Thr Glu Val Thr Tyr Thr Cys Ser Gly Asn
             100                 105                 110

Tyr Phe Leu Met Asp Pro Gln Asp Pro His Ala Glu His Lys Val Lys
```

-continued

```
                    115                 120                 125
Ile Gly Val Glu Gln Lys Tyr Gly Gln Phe Pro Gln Gly Thr Glu Val
        130                 135                 140
Thr Tyr Thr Cys Ser Gly Asn Tyr Phe Leu Met Asp
145                 150                 155

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:amino acids
      used to link S3 multimer to remainder of
      polypeptide

<400> SEQUENCE: 10

Ile Glu Gly Arg
  1

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:enterokinase
      recognition sequence, enterokinase cleavage site
<220> FEATURE:
<221> NAME/KEY: MOD_RES
<222> LOCATION: (1)..(7)
<223> OTHER INFORMATION: Xaa = any amino acid
<220> FEATURE:
<221> NAME/KEY: MOD_RES
<222> LOCATION: (4)..(5)
<223> OTHER INFORMATION: Asp at positions 4 and 5 may be present or
      absent

<400> SEQUENCE: 11

Xaa Asp Asp Asp Asp Lys Xaa
  1               5
```